United States Patent
Brown et al.

(10) Patent No.: US 6,498,274 B1
(45) Date of Patent: Dec. 24, 2002

(54) AMIDE DERIVATIVES FOR THE TREATMENT OF DISEASES MEDIATED BY CYTOKINES

(75) Inventors: Dearg S Brown, Macclesfield (GB); George R Brown, Macclesfield (GB); Philip Cohen, Dundee (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/508,055

(22) PCT Filed: Sep. 17, 1998

(86) PCT No.: PCT/GB98/02826

§ 371 (c)(1), (2), (4) Date: Mar. 7, 2000

(87) PCT Pub. No.: WO99/15164

PCT Pub. Date: Apr. 1, 1999

(30) Foreign Application Priority Data

Sep. 23, 1997 (GB) .............................. 9720120
May 15, 1998 (GB) .............................. 9810355

(51) Int. Cl.[7] .................. C07C 233/05; A61K 31/16
(52) U.S. Cl. .................. 564/157; 564/134; 564/138; 564/158; 546/207; 546/225; 544/111; 544/145; 514/252.12; 514/231.8; 514/232.5; 514/616
(58) Field of Search ..................... 514/616, 252.12, 514/231.8, 232.5; 564/134, 138, 158, 157; 546/207, 225; 544/111, 145

(56) References Cited

U.S. PATENT DOCUMENTS

| 1,903,899 A | 4/1933 | Laska et al. |
| 1,909,960 A | 5/1933 | Hitch |
| 4,749,729 A | 6/1988 | Kohli et al. |

FOREIGN PATENT DOCUMENTS

| DE | 28 12 252 | | 10/1979 |
| EP | 0 849 256 A1 | | 6/1998 |
| JP | 61-204221 | * | 9/1986 |
| WO | WO 93/04170 | | 3/1993 |
| WO | WO 97/05878 | | 2/1997 |
| WO | WO 97/32853 | | 9/1997 |
| WO | WO 98/06715 | | 2/1998 |
| WO | WO 98/22103 | | 5/1998 |
| WO | WO 99/15164 | | 4/1999 |
| WO | WO 99/59959 | | 11/1999 |
| WO | WO 99/59960 | | 11/1999 |
| WO | WO 00/07980 | | 2/2000 |
| WO | WO 00/07991 | | 2/2000 |
| WO | WO 00/18738 | | 4/2000 |
| WO | WO 00/20402 | | 4/2000 |
| WO | WO 00/55120 | | 9/2000 |
| WO | WO 00/55153 | | 9/2000 |
| WO | WO 99/56738 | | 9/2000 |
| WO | WO 01/27089 | | 4/2001 |

OTHER PUBLICATIONS

Database WPI Derwent Publication Ltd., London, GB; AN 323139 XP002086154 "New n-substituted cyclic carboxamide compounds are inflammatory cytokine inhibitors used as antiinflammatory agents" & JP 409 124 571 a (Japan Tobacco Inc) see abstract see examples: p. 56 and following.
Hanson G.J.: "inhibitors of p38 kinase" Expert Opinion on Therapeutic Patents, vol. 7, No. 7, 1997, pp. 729–733, XP002086152 cited in the application see the whole document.
Ashton et al: "now low-density lipoprotein receptor upregulators acting via a novel mechanism" J. Med. Chem., vol. 39, No. 17, 1996, pp. 3343–3356, XP002086153 cited in the application see pp. 3344–3346.
Ando et al., Magn. Reson.Chem. 639–45, 1995, Chemical Abstract: 123:227514, 1995 (need copy).
Ando et al., "Producing azo lake pigments"; Chemical Abstract, vol. 106, Abstract No. 215574.
Chemical Abstracts, vol. 51, columns 5067 and 5068 Ito et al., Photosensitive material containing microencapsulated hydrazine derivatives; Chemical Abstract, vol. 118, Abstract No. 70021.
Lesiak, "New amides of pyrrole-N- and indole-N-caboxylic acids", Chemical Abstracts, No. 126704v, XP-002121335.
Mühlbach, "Pyrazoles—A Novel Class of Blocking Agents for Isocyanates", Journal of Polymer Science: Part A: Polymer Chemistry, vol. 32, Mar. 1994, pp. 753–765.
Sugawara et al., Kogyo Kaguku Zasshi 72(11) 2425–2429, 1969, Chemical Abstract: 72:66514, 1970 (need copy).
Wang et al., "Low-valent Titanium-induced Reactions of Substituted Nitrobenzenes", J. Chem. Research, 1998, pp. 182–183.

* cited by examiner

*Primary Examiner*—Shailendra Kumar
(74) *Attorney, Agent, or Firm*—Morgan, Lewis & Bockius LLP

(57) ABSTRACT

The invention concerns the use of amide derivatives of formula (I) wherein: $R^1$ and $R^2$ are substituents such as hydroxy, $C_{1-6}$alkoxy, mercapto, $C_{1-6}$alkylthio, amino, $C_{1-6}$alkylamino and di-$(C_{1-6}$alkyl)amino; m and p are independently 0–3 $R^3$ is $C_{1-4}$alkyl; q is 0–4; and $R^4$ is aryl or cycloalkyl; or a pharmaceutically acceptable salt thereof in the manufacture of a medicament for use in the treatment of diseases or medical conditions mediated by cytokines

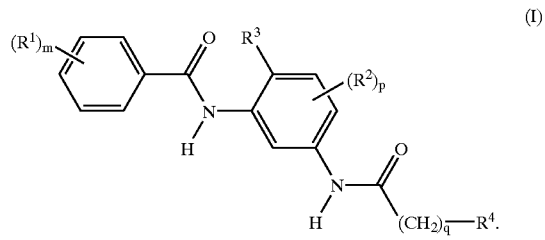

15 Claims, No Drawings

AMIDE DERIVATIVES FOR THE TREATMENT OF DISEASES MEDIATED BY CYTOKINES

This application is a 371 of PCT/GB98/02826, filed Sep. 17, 1998.

This invention concerns the use of certain amide derivatives as inhibitors of cytokine mediated disease. The invention also concerns certain novel amide derivatives, processes for the manufacture of said novel amide derivatives, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis and adult respiratory distress syndrome), and in the production and development of various cardiovascular and cerebrovascular disorders such as myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/ or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. P38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*, 1997, 7, 729–733. p38 kinase is known to exist in isoforms identified as p38α and p38β.

The compounds disclosed in the present invention are inhibitors of the production of cytokines such as TNF, in particular of TNFα, and various interleukins, in particular IL-1.

According to one aspect of the present invention there is provided the use of a compound of the Formula I

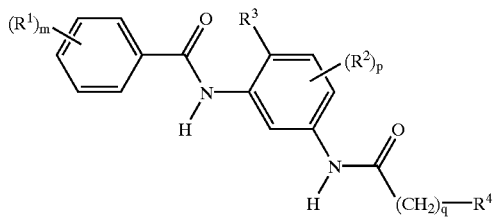

Formula I wherein:

$R^1$ and $R^2$, which may be the same or different are selected from hydroxy, $C_{1-6}$alkoxy, mercapto, $C_{1-6}$alkylthio, amino, $C_{1-6}$alkylamino, di-($C_{1-6}$alkyl)amino, carboxy, $C_{1-6}$alkoxycarbonyl, carbamoyl, $C_{1-6}$alkylcarbamoyl, di-$C_{1-6}$alkylcarbamoyl, $C_{1-6}$alkylsulphonyl, arylsulphonyl, $C_{1-6}$alkylaminosulphonyl, di-($C_{1-6}$alkyl)aminosulphonyl, nitro, cyano, cyano$C_{1-6}$alkyl, hydroxyC$_{1-6}$alkyl, aminoC$_{1-6}$alkyl, C$_{1-6}$alkanoylamino, C$_{1-6}$alkoxycarbonylamino, C$_{1-6}$alkanoyl, C$_{1-6}$alkanoyloxy, C$_{1-6}$alkyl, halo, trifluoromethyl, aryl, arylC$_{1-6}$alkyl, arylC$_{1-6}$alkoxy, heteroaryl, heteroarylC$_{1-6}$alkyl, heterocyclyl and heterocyclylC$_{1-6}$alkyl;

m and p, are independently 0–3, and when m and/or p is 2 or 3 each R group may be the same or different;

R$^3$ is C$_{1-4}$alkyl;

q is 0–4;

R$^4$ is aryl or cycloalkyl wherein R$^4$ is optionally substituted with up to 3 substituents having any value defined for R$^1$;

or a pharmaceutically-acceptable salt or in vivo cleavable ester thereof in the manufacture of a medicament for use in the treatment of diseases or medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in vivo cleavable ester thereof.

In a further aspect the present invention provides the use of a compound of the Formula I, or a pharmaceutically-acceptable salt or in vivo cleavable ester thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I, or a pharmaceutically-acceptable salt or in vivo cleavable ester thereof.

In a further aspect the present invention provides the use of a compound of the Formula I, or a pharmaceutically-acceptable salt or in vivo cleavable ester thereof, in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in vivo cleavable ester thereof.

In a further aspect the present invention provides the use of a compound of the Formula I, or a pharmaceutically-acceptable salt or in vivo cleavable ester thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt or in vivo cleavable ester thereof.

In a further aspect the present invention provides the use of a compound of the Formula I, or a pharmaceutically-acceptable salt or in vivo cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in vivo cleavable ester thereof.

In a further aspect the present invention provides the use of a compound of the Formula I, or a pharmaceutically-acceptable salt or in vivo cleavable ester thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in vivo cleavable ester thereof.

In a further aspect the present invention provides, the use of a compound of the Formula I, or a pharmaceutically-acceptable salt or in vivo cleavable ester thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt or in vivo cleavable ester thereof.

In a further aspect the present invention provides the use of a compound of the Formula I, or a pharmaceutically-acceptable salt or in vivo cleavable ester thereof, in the manufacture of a medicament for use in the treatment of rheumatoid arthritis, asthma, irritable bowel disease, multiple sclerosis, AIDS, septic shock, ischaemic heart disease or psoriasis.

In a further aspect the present invention provides a method of treating rheumatoid arthritis, asthma, irritable bowel disease, multiple sclerosis, AIDS, septic shock, ischaemic heart disease or psoriasis which comprises administering to a warm-blooded animal an effective amount of a compound of the Formula I, or a pharmaceutically-acceptable salt or in vivo cleavable ester thereof.

Certain compounds falling within the scope of Formula (I) are known to upregulate LDL receptors (Brown et al. in *Atherosclerosis* (1994) 109:113–114, Halley et al. in *J. Med. Chem.*, (1996) 39: 3343–3356). The compounds listed immediately hereinafter were disclosed in that *J. Med. Chem.* paper and fall within the scope of the compound definition disclosed hereinbefore:

N-[5-(3-cyclohexylpropionamido)-2-methylphenyl]-4-hydroxybenzamide, N-[5-(3-cyclohexylpropionamido)-2-methylphenyl]-4-acetoxybenzamide, N-[5-(3-cyclohexylpropionamido)-2-methylphenyl]benzamide, N-[5-(3-cyclohexylpropionamido)-2-methylphenyl]-3-hydroxybenzamide, N-[5-(3-cyclohexylpropionamido)-2-methylphenyl]-2-hydroxybenzamide, N-[5-(3-cyclohexylpropionamido)-2-methylphenyl]-4-methoxycarbonylbenzamide, N-[5-(3-cyclohexylpropionamido)-2-methylphenyl]-4-hydroxymethylbenzamide, N-[5-(3-cyclohexylpropionamido)-2-methylphenyl]-4-nitrobenzamide, N-[5-(3-cyclohexylpropionamido)-2-methylphenyl]-4-aminobenzamide, N-[5-(2-cyclohexylacetamido)-2-methylphenyl]-4-acetoxybenzamide, N-[5-(4-cyclohexylbutyrylamino)-2-methylphenyl]-4-hydroxybenzamide, N-[5-(3-cyclopentylpropionamido)-2-methylphenyl]-4-hydroxybenzamide, N-[5-(3-phenylpropionamido)-2-methylphenyl]-4-hydroxybenzamide, N-[5-(4-cyclohexylbutyrylamino)-2-methylphenyl]-4-acetoxybenzamide, N-[5-(3-phenylpropionamido)-2-methylphenyl]-4-acetoxybenzamide and N-[5-(3-cyclopentylpropionamido)-2-methylphenyl]-4-acetoxybenzamide.

From these compounds the following representative examples have now been found to possess p38 kinase inhibitory activity:

N-[5-(3-cyclopentylpropionamido)-2-methylphenyl]-4-hydroxybenzamide, N-[5-(3-cyclohexylpropionamido)-2-methylphenyl]-3-hydroxybenzamide, N-[5(3-cyclohexylpropionamido)-2-methylphenyl]-4-hydroxybenzamide, N-[5-(3-cyclohexylpropionamido)-2-methylphenyl]-4-aminobenzamide and N-[5-(4-cyclohexylbutyrylamino)-2-methylphenyl]-4-hydroxybenzamide.

Copending International Patent Application PCT/GB97/03102 which gave rise on May 28, 1998 to International Application Publication No. WO 98/22103 concerns certain bisamide derivatives which are stated to possess inhibitory activity against the enzyme raf kinase and thereby to be useful in the treatment of diseases such as cancer. The compounds disclosed therein as examples are listed immediately hereinafter and fall within the scope of the compound definition disclosed hereinbefore:

N-[5-(2-bicyclo[2.2.1]hept-2-ylacetamido)-2-methylphenyl]-4-hydroxybenzamide, N-{5-[2-(3,4-dichlorophenyl)acetamido]-2-methylphenyl}-4-hydroxybenzamide and N-[5-(3-dimethylaminobenzamido)-2-methylphenyl]-4-hydroxybenzamide. These compounds have now been found to possess p38 kinase inhibitory activity.

In a further aspect the present invention provides a compound of the Formula I as defined hereinbefore for use in a method of treatment of the human or animal body by therapy, in particular for use in the treatment of diseases or medical conditions mediated by cytokines and, more particularly, for use in inhibiting TNF, except that N-[5-(3-cyclohexylpropionamido)-2-methylphenyl]-4-hydroxybenzamide, N-[5-(3-cyclohexylpropionamido)-2-methylphenyl]-4-acetoxybenzamide, N-[5-(3-clohexylpropionamido)-2-methylphenyl]benzamide, N-[5-(3-cyclohexylpropionamido)-2-methylphenyl]-3-hydroxybenzamide, N-[5-(3-cyclohexylpropionamido)-2-methylphenyl]-2-hydroxybenzamide, N-[5-(3-cyclohexylpropionamido)-2-methylphenyl]-4-methoxycarbonylbenzamide, N-[5-(3-cyclohexylpropionamido)-2-methylphenyl]-4-hydroxymethylbenzamide, N-[5-(3-cyclohexylpropionamido)-2-methylphenyl]-4-nitrobenzamide, N-[5-(3-cyclohexylpropionamido)-2-methylphenyl]-4-aminobenzamide, N-[5-(2-cyclohexylacetamido)-2-methylphenyl]-4-acetoxybenzamide, N-[5-(4-cyclohexylbutyrylamino)-2-methylphenyl]-4-hydroxybenzamide, N-[5-(3-cyclopentylpropionamido)-2-methylphenyl]-4-hydroxybenzamide, N-[5-(3-phenylpropionamido)-2-methylphenyl]-4-hydroxybenzamide, N-[5-(2-bicyclo[2.2.1]hept-2-ylacetamido)-2-methylphenyl]-4-hydroxybenzamide, N-{5-[2-(3,4-dichlorophenyl)acetamido]-2-methylphenyl}-4-hydroxybenzamide, N-[5-(3-dimethylaminobenzamido)-2-methylphenyl]-4-hydroxybenzamide, N-[5-(4-cyclohexylbutyrylamino)-2-methylphenyl]-4-acetoxybenzamide, N-[5-(3-phenylpropionamido)-2-methylphenyl]-4-acetoxybenzamide and N-[5-(3-cyclopentylpropionamido)-2-methylphenyl]-4-acetoxybenzamide are excluded.

Certain other compounds within the scope of Formula I are known outside the pharmaceutical field:

(a) Japanese Patent Application No. 04065513 (Chemical Abstracts, 117, 50742) discloses the compound N-[5-(4-carbamoylbenzamido)-2-methylphenyl]-4-carbamoylbenzamide as a chemical intermediate;

(b) Japanese Patent Application No. 62198852 (Chemical Abstracts, 109, 14765) discloses the compound N-[5-(3,4,5-trihydroxybenzamido)-2-methylphenyl]-3,4,5-trihydroxybenzamide as a chemical intermediate;

(c) U.S. Pat. No. 4,410,681 (Chemical Abstracts, 100, 52612) and U.S. Pat. No. 4,367,328 (Chemical Abstracts, 98, 144515) each disclose the compound N-[5-(2-hydroxybenzamido)-2-methylphenyl]-2-hydroxybenzamide as a chemical intermediate;

(d) Japanese Patent Application No. 53079835 (Chemical Abstracts, 89, 147671) discloses the compound N-{5-[4-carboxy-3-(2-dimethylaminoethoxycarbonyl)benzamido]-2-methylphenyl}-4-carboxy-3-(2-dimethylaminoethoxycarbonyl)benzamide as a chemical intermediate;

(e) German Patent Application No. DE 2552609 (Chemical Abstracts, 85, 192408) discloses the compounds N-[5-(3-methoxycarbonylbenzamido)-2-methylphenyl]-3-methoxycarbonylbenzamide and N-[5-(4-methoxycarbonylbenzamido)-2-methylphenyl]-4-methoxycarbonylbenzamide as chemical intermediates;

(f) Japanese Patent Application No. 50105558 (Chemical Abstracts, 84, 45269) discloses the compound N-[5-(4-methoxybenzamido)-2-methylphenyl]-4-methoxybenzamide as a chemical intermediate;

(g) Japanese Patent Application No. 61204221 (Chemical Abstracts, 106, 34087) discloses the compound N-(5-benzamido-2-methylphenyl)benzamide as a chemical intermediate;

(h) Netherlands Patent Application No. 6514411 (Chemical Abstracts, 65, 10706f) discloses certain indolizine derivatives as aromatic pigments;

(i) Chemical Abstracts, 64, 19459g concerns reduction of some alkyl-substituted dinitrobenzenes and discloses the compound N-(5-benzamido-2-ethylphenyl)benzamide; and (j) Chemical Abstracts, 62, 3959d discloses the compound N-[5-(4-nitrobenzamido)-2-ethylphenyl]-4-nitrobenzamide.

The reader is directed to these references for general guidance on synthesis of compounds within the scope of Formula I.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

"Aryl" in terms such as "aryl", "arylC$_{1-6}$alkyl", "arylsulphonyl" and "arylC$_{1-6}$alkoxy" typically means phenyl or naphthyl, preferably phenyl. An "arylC$_{1-6}$alkyl" group means, for example, arylmethyl or 2-arylethyl. An "arylC$_{1-6}$alkoxy" group means, for example, arylmethoxy or 2-arylethoxy. "Heteroaryl" in the terms "heteroaryl" and "heteroarylC$_{1-6}$alkyl" means an aromatic mono- or bicyclic 5–10 membered ring with up to five ring heteroatoms selected from nitrogen, oxygen and sulphur. Examples of 'heteroaryl' include thienyl, pyrrolyl, furyl, imidazolyl, oxazolyl, thiazolyl, pyrazolyl, isoxazolyl, isothiazolyl, oxadiazolyl, thiadiazolyl, triazolyl, tetrazolyl, pyrazinyl, pyridazinyl, pyrimidinyl, pyridyl, indolyl, benzofuranyl, benzothienyl, benzimidazolyl benzoxazolyl, benzothiazolyl, indazolyl, quinolyl, isoquinolyl, quinazolinyl, quinoxalinyl and cinnolinyl. A "heteroaryl$C_{1-6}$alkyl" group means, for example, heteroarylmethyl or 2-heteroarylethyl. "Heterocyclyl" in the terms "heterocyclyl" and "heterocyclyl$C_{1-6}$ alkyl" means a non-aromatic mono- or bicyclic 5–10 membered ring with up to five ring hetero atoms selected from nitrogen, oxygen and sulphur. Examples of 'heterocyclyl' include pyrrolinyl, pyrrolidinyl, morpholinyl, piperidinyl, piperazinyl, homopiperidinyl, homopiperazinyl, dihydropyridinyl, tetrahydropyridinyl, dihydropyrimidinyl and tetrahydropyrimidinyl. A "heterocyclyl$C_{1-6}$alkyl" group means, for example, heterocyclylmethyl or 2-heterocyclylethyl. "Cycloalkyl" means a non-aromatic mono- or bicyclic 5–10 membered carbon ring. Examples of "cycloalkyl" include cyclopentyl, cyclohexyl, cycloheptyl, bicyclo[2.2.1]heptyl and bicyclo[4.4.0]decyl.

Typical values for other generic groups include: for $C_{1-6}$alkoxy, for example, methoxy and ethoxy, for $C_{1-6}$alkylthio, for example, methylthio, for $C_{1-6}$alkylamino, for example, methylamino, for di-($C_{1-6}$alkyl)amino, for example, dimethylamino, for $C_{1-6}$alkoxycarbonyl, for example, methoxycarbonyl and ethoxycarbonyl, for $C_{1-6}$alkylcarbamoyl, for example, methylcarbamoyl, for di-$C_{1-6}$alkylcarbamoyl, for example, dimethylcarbamoyl, for $C_{1-6}$alkylsulphonyl, for example, methylsulphonyl, for arylsulphonyl, for example, phenylsulphonyl, for $C_{1-6}$alkylaminosulphonyl, for example, methylaminosulphonyl, for di-($C_{1-6}$alkyl)aminosulphonyl, for example, dimethylaminosulphonyl, for cyano$C_{1-6}$alkyl, for example, cyanomethyl, for hydroxy$C_{1-6}$alkyl, for example, hydroxymethyl, for amino$C_{1-6}$alkyl, for example, aminomethyl, for $C_{1-6}$alkanoylamino, for example, formamido and acetamido, for $C_{1-6}$alkoxycarbonylamino, for example, methoxycarbonylamino, for $C_{1-6}$alkanoyl, for example, formyl and acetyl, for $C_{1-6}$alkanoyloxy, for example, acetoxy, for $C_{1-6}$alkyl or $C_{1-4}$alkyl, for example, methyl, ethyl, propyl, isopropyl and tert-butyl, for halo, for example, fluoro, chloro and bromo, for aryl, for example, phenyl, for aryl$C_{1-6}$alkyl, for example, benzyl, and for aryl$C_{1-6}$alkoxy, for example, benzyloxy.

Any ring in $R^1$ or $R^2$ or any ring in a substituent on $R^4$ may be optionally substituted, for example by up to 3 substituents. Suitable substituents include hydroxy, $C_{1-6}$alkoxy, mercapto, $C_{1-6}$alkylthio, amino, $C_{1-6}$alkylamino, di-($C_{1-6}$alkyl)amino, carboxy, carbamoyl, $C_{1-6}$alkylcarbamoyl, di-$C_{1-6}$alkylcarbamoyl, $C_{1-6}$alkylsulphonyl, arylsulphonyl, $C_{1-6}$alkylaminosulphonyl, di-($C_{1-6}$alkyl)aminosulphonyl, nitro, cyano, cyano$C_{1-6}$alkyl, hydroxy$C_{1-6}$alkyl, amino$C_{1-6}$ alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, halo and trifluoromethyl. For example, when $R^1$ or a substituent on $R^4$ is a heterocyclyl or heterocyclyl$C_{1-6}$alkyl group the heterocyclyl ring may bear up to 3 substituents selected from hydroxy, $C_{1-6}$alkoxy, carboxy, carbamoyl, $C_{1-6}$alkylcarbamoyl, di-$C_{1-6}$alkylcarbamoyl, $C_{1-6}$alkanoyl, $C_{1-6}$alkyl, halo and trifluoromethyl. Examples of such substituted heterocyclyl rings include 4-carbamoylpiperidin-1-yl, 4-methylpiperazin-1-yl and 4-acetylpiperazin-1-yl.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Preferably $R^1$ is hydroxy, $C_{1-6}$alkoxy, $C_{1-6}$alkoxycarbonyl, carbamoyl, $C_{1-6}$alkylcarbamoyl, $C_{1-6}$alkanoylamino, $C_{1-6}$alkanoyl, $C_{1-6}$alkanoyloxy, $C_{1-6}$alkyl, halo, trifluoromethyl, phenyl or phenyl $C_{1-6}$alkoxy.

Most preferably $R^1$ is hydroxy, $C_{1-6}$alkoxy, $C_{1-6}$alkanoylamino or $C_{1-6}$alkanoyl.

Preferably m is 1 or 2.

Preferably $R^3$ is methyl.

Preferably $R^2$ is carboxy, $C_{1-6}$alkoxycarbonyl, carbamoyl, $C_{1-6}$alkylcarbamoyl or di-($C_{1-6}$alkyl)carbamoyl.

Preferably p is 0.

Preferably $R^4$ is phenyl, cyclohexyl or cyclopentyl.

More preferably $R^4$ is phenyl or cyclohexyl.

Preferred substituents for aryl and cyclohexyl groups in $R^4$ are hydroxy, $C_{1-6}$alkoxy, $C_{1-6}$alkoxycarbonyl, carbamoyl, $C_{1-6}$alkylcarbamoyl, $C_{1-6}$alkanoylamino, $C_{1-6}$alkanoyl, $C_{1-6}$alkanoyloxy, $C_{1-6}$alkyl, halo, trifluoromethyl, phenyl, phenyl$C_{1-6}$alkoxy, nitro, cyano, amino, $C_{1-6}$alkylamino or di-($C_{1-6}$alkyl)amino.

More preferably substituents for aryl and cyclohexyl in $R^4$ are selected from cyano. dimethylamino, methoxy, ethoxy, fluoro, chloro, nitro and phenyl.

In a further aspect the present invention provides novel compounds within the scope of the compounds of the Formula I as defined hereinbefore.

A particular group of compounds of the invention includes, for example, amide derivatives of the Formula I, or pharmaceutically-acceptable salts thereof, wherein:

(a) q is 1, 2, 3 or 4 and $R^4$ is cycloalkyl, and $R^1$, $R^2$, $R^3$, m and p have any of the meanings defined hereinbefore; and (b) q is 0 and $R^4$ is phenyl which is optionally substituted with up to 3 substituents having any value defined hereinbefore for $R^1$; and $R^1$, $R^2$, $R^3$, m and p have any of the meanings defined hereinbefore.

A particular novel compound of the invention is an amide derivative of the Formula I wherein $R^1$ is hydroxy, methoxy, ethoxy, propoxy, isopropoxy, butoxy, amino, methylamino, dimethylamino, carboxy, methoxycarbonyl, nitro, cyano, acetamido, acetyl, acetoxy, methyl, ethyl, propyl, isopropyl, butyl, tert-butyl, fluoro, chloro, bromo, trifluoromethyl, pyrrolidin-1-yl, piperidino, morpholino, 4-thiamorpholino, piperazin-1-yl, 4-methylpiperazin-1-yl, 4-methylhomopiperazin-1-yl, pyrrolidin-1-ylmethyl, piperidinomethyl, 4-carbamoylpiperidin-1-ylmethyl, morpholinomethyl, 4-thiamorpholinomethyl, piperazin-1-ylmethyl, 4-methylpiperazin-1-ylmethyl, 4-ethylpiperazin-1-ylmethyl, 4-propylpiperazin-1-ylmethyl, 4-isopropylpiperazin-1-ylmethyl, 4-acetylpiperazin-1-ylmethyl and 4-methylhomopiperazin-1-ylmethyl;

m is 1, 2 or 3;

p is 0;

$R^3$ is methyl;

q is 0; and $R^4$ is phenyl which is optionally substituted with 1 or 2 substituents selected from hydroxy, methoxy, ethoxy, amino, methylamino, dimethylamino, methoxycarbonyl, nitro, cyano, acetamido, fluoro, chloro, bromo, trifluoromethyl, phenyl, benzyloxy, pyrrolidin-1-yl, piperidino morpholino, 4-thiamorpholino, piperazin-1-yl, 4-methylpiperazin-1-yl, 4-methylhomopiperazin-1-yl, pyrrolidin-1-ylmethyl, piperidinomethyl, 4-carbamoylpiperidin-1-ylmethyl, morpholinomethyl, 4-thiamorpholinomethyl, piperazin-1-ylmethyl, 4-methylpiperazin-1-ylmethyl, 4-ethylpiperazin-1-ylmethyl, 4-propylpiperazin-1-ylmethyl, 4-isopropylpiperazin-1-ylmethyl, 4-acetylpiperazin-1-ylmethyl and 4-methylbomopiperazin-1-ylmethyl;

or a pharmaceutically-acceptable salt thereof;

except that N-[5-(3-dimethylaminobenzamido)-2-methylphenyl]-4-hydroxybenzamide, N-[5-(2-hydroxybenzamido)-2-methylphenyl]-2-hydroxybenzamide, N-[5-(4-methoxybenzamido)-2-methylphenyl]-4-methoxybenzamide, N-[5-(3-methoxycarbonylbenzamido)-2-methylphenyl]-3-methoxycarbonylbenzamide and N-[5(4-methoxycarbonylbenzamido)-2-methylphenyl]-4-methoxycarbonylbenzamide are excluded.

A preferred novel compound of the invention is an amide derivative of the Formula I wherein $R^1$ is hydroxy, methoxy, ethoxy, isopropoxy, carboxy, methoxycarbonyl, nitro, cyano, acetyl, acetoxy, methyl, ethyl, propyl, fluoro, chloro or trifluoromethyl;

m is 1, 2 or 3;

p is 0;

$R^3$ is methyl;

q is 0; and $R^4$ is phenyl which is optionally substituted with 1 or 2 substituents selected from hydroxy, methoxy, amino, methylamino, dimethylamino, nitro, cyano, fluoro, chloro, bromo, trifluoromethyl and benzyloxy;

or a pharmaceutically-acceptable salt thereof;

except that N-[5-(3-dimethylaminobenzamido)-2-methylphenyl]-4-hydroxybenzamide, N-[5-(2-hydroxybenzamido)-2-methylphenyl]-2-hydroxybenzamide and N-[5-(4-methoxybenzamido)-2-methylphenyl]-4-methoxybenzamide are excluded.

A more preferred novel compound of the invention is an amide derivative of the Formula I
wherein $R^1$ is hydroxy, methoxy, carboxy or acetoxy;

m is 1 or 2;

p is 0;

$R^3$ is methyl;

q is 0; and $R^4$ is phenyl which is optionally substituted with a substituent selected from hydroxy, dimethylamino, cyano and benzyloxy;

or a pharmaceutically-acceptable salt thereof;

except that N-[5-(3-dimethylaminobenzamido)-2-methylphenyl]-4-hydroxybenzamide and N-[5-(2-hydroxybenzamido)-2-methylphenyl]-2-hydroxybenzamide are excluded.

A further preferred novel compound of the invention is an amide derivative of the Formula I wherein $R^1$ is hydroxy, methoxy, ethoxy, propoxy, isopropoxy, butoxy, amino, methylamino, dimethylamino, carboxy, methoxycarbonyl, nitro, cyano, acetamido, acetyl, acetoxy, methyl, ethyl, propyl, isopropyl, butyl, tert-butyl, fluoro, chloro, bromo, trifluoromethyl, pyrrolidin-1-yl, piperidino, morpholino, 4-thiamorpholino, piperazin-1-yl, 4-methylpiperazin-1-yl, 4-methylhomopiperazin-1-yl, pyrrolidin-1-ylmethyl, piperidinomethyl, 4-carbamoylpiperidin-1-ylmethyl, morpholinomethyl, 4-thiamorpholinomethyl, piperazin-1-ylmethyl, 4-methylpiperazin-1-ylmethyl, 4-ethylpiperazin-1-ylmethyl, 4-propylpiperazin-1-ylmethyl, 4-isopropylpiperazin-1-ylmethyl, 4-acetylpiperazin-1-ylmethyl and 4-methylhomopiperazin-1-ylmethyl;

m is 1, 2 or 3;

p is 0;

$R^3$ is methyl;

q is 1, 2, 3 or 4; and $R^4$ is cyclopentyl or cyclohexyl;

or a pharmaceutically-acceptable salt thereof;

except that N-[5-(3-cyclohexylpropionamido)-2-methylphenyl]-4-hydroxybenzamide. N-[5-(3-cyclohexylpropionamido)-2-methylphenyl]-4-acetoxybenzamide, N-[5-(3-cyclohexylpropionamido)-2-methylphenyl]-3-hydroxybenzamide, N-[5-(3-cyclohexylpropionamido)-2-methylphenyl]-2-hydroxybenzamide, N-[5-(3-cyclohexylpropionamido)-2-methylphenyl]-4-hydroxybenzamide, N-[5-(3-cyclohexylpropionamido)-2-methylphenyl]-4-nitrobenzamide, N-[5-(3-cyclohexylpropionamido)-2-methylphenyl]-4-aminobenzamide, N-[5-(2-cyclohexylacetamido)-2-methylphenyl]-4-acetoxybenzamide, N-[5-(4-cyclohexylbutyrylamino)-2-methylphenyl]-4-hydroxybenzamide, N-[5-(3-cyclopentylpropionamido)-2-methylphenyl]-4-hydroxybenzamide, N-[5-(4-cyclohexylbutyrylamino)-2-methylphenyl]-4-acetoxybenzamide and N-[5-(3-cyclopentylpropionamido)-2-methylphenyl]-4-acetoxybenzamide are excluded.

A further preferred novel compound of the invention is an amide derivative of the Formula I wherein $R^1$ is hydroxy, methoxy, ethoxy, isopropoxy, carboxy, methoxycarbonyl, nitro, cyano, acetyl, acetoxy, methyl, ethyl, propyl, fluoro, chloro or trifluoromethyl;

m is 1, 2 or 3;

p is 0;

$R^3$ is methyl;

q is 1, 2, 3 or 4; and $R^4$ is cyclohexyl;

or a pharmaceutically-acceptable salt thereof;

except that N-[5-(3-cyclohexylpropionamido)-2-methylphenyl]-4-hydroxybenzamide, N-5-(3-cyclohexylpropionamido)-2-methylphenyl]-4-acetoxybenzamide, N-[5-(3-cyclohexylpropionamido)-2-methylphenyl]-3-hydroxybenzamide, N-[5-(3-cyclohexylpropionamido)-2-methylphenyl]-2-hydroxybenzamide, N-[5-(3-cyclohexylpropionamido)-2-methylphenyl]-4-methoxycarbonylbenzamide, N-[5-(3-cyclohexylpropionamido)-2-methylphenyl]-4-nitrobenzamide, N-[5-(2-cyclohexylacetamido)-2-methylphenyl]-4-acetoxybenzamide, N-[5-(4-cyclohexylbutyrylamino)-2-methylphenyl]-4-hydroxybenzamide, N-[5-(4-cyclohexylbutyrylamino)-2-methylphenyl]-4-acetoxybenzamide and N-[5-(4-cyclohexylbutyrylamino)-2-methylphenyl]-4-acetoxybenzamide are excluded.

A further more preferred novel compound of the invention is an amide derivative of the Formula I wherein $R^1$ is hydroxy, methoxy, carboxy or acetoxy;

m is 1 or 2;

p is 0;

R³ is methyl;

q is 2, 3, or 4; and

R⁴ is cyclohexyl;

or a pharmaceutically-acceptable salt thereof;

except that N-[5-(3-cyclohexylpropionamido)-2-methylphenyl]-4-hydroxybenzamide, N-[5-(3-cyclohexylpropionamido)-2-methylphenyl]-4-acetoxybenzamide, N-[5-(3-cyclohexylpropionamido)-2-methylphenyl]-3-hydroxybenzamide, N-[5-(3-cyclohexylpropionamido)-2-methylphenyl]-2-hydroxybenzamide, N-[5-(4-cyclohexylbutyrylamino)-2-methylphenyl]-4-hydroxybenzamide and N-[5-(4-cyclohexylbutyrylamino)-2-methylphenyl]-4-acetoxybenzamide are excluded.

Particular compounds for use in the present invention are:

N-[5-(4-cyclohexylbutyrylamino)-2-methylphenyl]-4-hydroxybenzamide;

N-[5-(4-cyanobenzamido)-2-methylphenyl]-4-hydroxybenzamide;

N-[5-(5-cyclohexylvalerylamino)-2-methylphenyl]-4-hydroxybenzamide;

N-[5-(3-cyclohexylpropionamido)-2-methylphenyl]-4-hydroxybenzamide;

N-[5-(3-dimethylaminobenzamido)-2-methylphenyl]-4-hydroxybenzamide;

N-(5-benzamido-2-methylphenyl)-4-hydroxybenzamide;

N-[5-(2-(3,4-dichlorophenyl)acetamido)-2-methylphenyl]-4-hydroxybenzamide;

N-[5-(3,5-dimethoxybenzamido)-2-methylphenyl]-4-hydroxybenzamide;

N-[5-(2-fluoro-6-chlorobenzamido)-2-methylphenyl]-4-hydroxybenzamide;

N[5-(3-cyclopentylpropionamido)-2-methylphenyl]-4-hydroxybenzamide;

N-[5-(4-phenylbenzamido)-2-methylphenyl]-4-hydroxybenzamide;

N-[5-(2-(4-nitrophenyl)acetamido)-2-methylphenyl]-4-hydroxybenzamide;

N-[5-(2-cyclohexylpropionamido)-2-methylphenyl]-4-acetylbenzamide;

N-[5-(3-dimethylaminobenzamido)-2-methylphenyl]-3,4-dimethoxybenzamide;

N-[5-(3-dimethylaminobenzamido)-2-methylphenyl]-4-methoxybenzamide;

N-[5-(3-cyclohexylpropionamido)-2-methylphenyl]-4-hydroxy-3-methoxybenzamide;

N-[5-(3-cyclohexylpropionamido)-2-methylphenyl]-3,4-dimethoxybenzamide:

N-[5-(3-cyclohexylpropionamido)-2-methylphenyl]-4-methoxybenzamide;

N-[5-(3-cyclohexylpropionamido)-2-methylphenyl]-3-hydroxybenzamide; and

N-[5-(3-cyclohexylpropionamido)-2-methylphenyl]-2-acetamidobenzamide;

and pharmaceutically-acceptable salts thereof.

Particular novel compounds of the present invention are:

N-[5-(3-benzyloxybenzamido)-2-methylphenyl]-3,4-dimethoxybenzamide;

N-[5-(4-cyanobenzamido)-2-methylphenyl]-4-acetoxybenzamide;

N-(5-benzamido-2-methylphenyl)-3,4-dimethoxybenzamide;

N-[5-(4-cyanobenzamido)-2-methylphenyl]-3,4-dimethoxybenzamide;

N-[5-(3-hydroxybenzamido)-2-methylphenyl]-3,4-dimethoxybenzamide;

N-[5-(3-dimethylaminobenzamido)-2-methylphenyl]-4-butoxybenzamide;

N-[5-(3-cyclohexylpropionamido)-2-methylphenyl]-3,4,5-trimethoxybenzamide; and

N-[5-(3-cyclohexylpropionamido)-2-methylphenyl]-4-carboxybenzamide;

and pharmaceutically-acceptable salts thereof.

A further particular novel compound of the present invention is:

N-[2-methyl-5-(3-trifluoromethylbenzamido)phenyl]-3,4-dimethoxybenzamide, and pharmaceutically-acceptable salts thereof.

In a further aspect of the present invention there is provided a group of novel compounds of the Formula I wherein R⁴ is phenyl which bears a basic substituent located at the 3- and/or 4-positions. This group of compounds possesses improved TNFα inhibitory potency in one or both of the PBMC and Human Whole Blood tests described hereinafter.

A particular group of novel compounds according to this aspect of the invention is an amide derivative of the Formula I wherein R¹ is hydroxy, $C_{1-6}$alkoxy, carboxy, $C_{1-6}$alkoxycarbonyl, nitro, cyano, $C_{1-6}$alkanoylamino, $C_{1-6}$alkanoyl, $C_{1-6}$alkyl, halo or trifluoromethyl;

m is 0–3 and when m is 2 or 3 each R¹ group is the same or different;

p is 0;

R³ is methyl;

q is 0; and

R⁴ is phenyl which is substituted with 1 or 2 substituents selected from amino, $C_{1-6}$alkylamino, di-($C_{1-6}$alkyl)amino, amino$C_{1-6}$alkyl, heteroaryl, heteroaryl$C_{1-6}$alkyl, heterocyclyl and heterocyclyl$C_{1-6}$alkyl, and when there is 1 substituent it is located at the 3-position and when there are 2 substituents, which may be the same or different, they are located at the 3- and 4-positions;

or a pharmaceutically-acceptable salt thereof;

except that N-[5-(3-dimethylaminobenzamido)-2-methylphenyl]-4-hydroxybenzamide is excluded.

A preferred group of novel compounds according to this aspect of the invention is an amide derivative of the Formula I wherein R¹ is hydroxy, methoxy, ethoxy, propoxy, isopropoxy, butoxy, carboxy, methoxycarbonyl, nitro, cyano, acetamido, acetyl, methyl, ethyl, propyl, isopropyl, butyl, tert-butyl, fluoro, chloro, bromo or trifluoromethyl;

m is 0–3 and when m is 2 or 3 each R¹ group is the same or different;

p is 0;

R³ is methyl;

q is 0; and

R⁴ is phenyl which is substituted at the 3- or 4-position with a substituent selected from amino, methylamino, dimethylamino, aminomethyl, pyrrolidin-1-yl, piperidino, morpholino, 4-thiamorpholino, piperazin-1-yl, 4-methylpiperazin-1-yl, 4-methylhomopiperazin- 1-yl, pyrrolidin-1-ylmethyl, piperidinomethyl, 4-carbamoylpiperidin-1-ylmethyl, morpholinomethyl, 4-thiamorpholinomethyl, piperazin-1-ylmethyl, 4-methylpiperazin-1-ylmethyl, 4-ethylpiperazin-1-ylmethyl, 4-propylpiperazin-1-ylmethyl, 4-isopropylpiperazin-1-ylmethyl, 4-acetylpiperazin-1-ylmethyl and 4-methylhomopiperazin-1-ylmethyl;

or a pharmaceutically-acceptable salt thereof;

except that N-[5-(3-dimethylaminobenzamido)-2-methylphenyl]-4-hydroxybenzamide is excluded.

A more preferred group of novel compounds according to this aspect of the invention is an amide derivative of the Formula I wherein $(R^1)_m$ is 3,4-dimethoxy or 3,4,5-trimethoxy;

p is 0;

$R^3$ is methyl;

q is 0; and $R^4$ is phenyl which is substituted at the 3-position with a substituent selected from dimethylamino, morpholino, morpholinomethyl, piperazin-1-ylmethyl and 4-methylpiperazin-1-ylmethyl;

or a pharmaceutically-acceptable salt thereof.

A particular novel compound of this aspect of the present invention is:

N-[2-methyl-5-(3-morpholinobenzamido)phenyl]-3,4,5-trimethoxybenzamide, and pharmaceutically-acceptable salts thereof.

In a further aspect of the present invention there is provided a group of novel compounds of the Formula I wherein $R^1$ is a basic substituent located at the 3- and/or 4-positions. This group of compounds possesses improved TNFα inhibitory potency in one or both of the PBMC and Human Whole Blood tests described hereinafter.

A particular group of novel compounds according to this aspect of the invention is an amide derivative of the Formula I wherein $R^1$ is amino, $C_{1-6}$alkylamino, di-($C_{1-6}$alkyl)amino, amino$C_{1-6}$alkyl, heteroaryl, heteroaryl$C_{1-6}$alkyl, heterocyclyl or heterocyclyl$C_{1-6}$alkyl;

m is 1 with the $R^1$ group located at the 3-position or m is 2 with the $R^1$ groups, which may be the same or different, located at the 3- and 4-positions;

p is 0;

$R^3$ is methyl;

q is 0; and $R^4$ is phenyl which is optionally substituted with 1 or 2 substituents, which may be the same or different, selected from hydroxy, $C_{1-6}$alkoxy, carboxy, $C_{1-6}$alkoxycarbonyl, cyano, $C_{1-6}$alkyl, halo and trifluoromethyl;

or a pharmaceutically-acceptable salt thereof.

A preferred group of novel compounds according to this aspect of the invention is an amide derivative of the Formula I wherein $R^1$ is amino, methylamino, dimethylamino, aminomethyl, pyrrolidin-1-yl, piperidino, morpholino, 4-thiamorpholino, piperazin-1-yl, 4-methylpiperazin-1-yl, 4-methylhomopiperazin-1-yl, pyrrolidin-1-ylmethyl, piperidinomethyl, 4-carbamoylpiperidin-1-ylmethyl, morpholinomethyl, 4-thiamorpholinomethyl, piperazin-1-ylmethyl, 4-methylpiperazin-1-ylmethyl, 4-ethylpiperazin-1-ylmethyl, 4-propylpiperazin-1-ylmethyl, 4-isopropylpiperazin-1-ylmethyl, 4-acetylpiperazin-1-ylmethyl or 4-methylhomopiperazin-1-ylmethyl;

m is 1 with the $R^1$ group located at the 3- or 4-position;

p is 0;

$R^3$ is methyl;

q is 0; and $R^4$ is phenyl which is optionally substituted with 1 or 2 substituents, which may be the same or different, selected from hydroxy, methoxy, ethoxy, carboxy, methoxycarbonyl, cyano, methyl, fluoro, chloro and trifluoromethyl;

or a pharmaceutically-acceptable salt thereof.

A more preferred group of novel compounds according to this aspect of the invention is an amide derivative of the Formula I wherein $R^1$ is morpholino, morpholinomethyl, piperazin-1-ylmethyl or 4-methylpiperazin-1-ylmethyl;

m is 1 with the $R^1$ group located at the 3-position;

p is 0;

$R^3$ is methyl;

q is 0; and $R^4$ is phenyl which is optionally substituted with 1 or 2 substituents, which may be the same or different, selected from methoxy, ethoxy, cyano, fluoro, chloro and trifluoromethyl;

or a pharmaceutically-acceptable salt thereof.

Particular novel compounds of this aspect of the present invention are:

N-(5-benzamido-2-methylphenyl)-3-(piperazin-1-yl)methylbenzamide, N-(5-benzamido-2-methylphenyl)-3-(4-methylpiperazin-1-yl)methylbenzamide, N-[2-methyl-5-(3-trifluoromethylbenzamido)phenyl]-3-(4-methylpiperazin-1-yl)methylbenzamide, N-[5-(3-chlorobenzamido)-2-methylphenyl]-3-(4-methylpiperazin-1-yl)methylbenzamide, N-[5-(2-methoxybenzamido)-2-methylphenyl]-3-(4-methylpiperazin-1-yl)methylbenzamide and N-[5-(3-ethoxybenzamido)-2-methylphenyl]-3-(4-methylpiperazin-1-yl)methylbenzamide;

and pharmaceutically-acceptable salts thereof.

In yet another aspect of the present invention there is provided a group of novel compounds of the Formula I wherein $(R^1)_m$ represents a basic substituent located at the 3- and/or 4-positions and $R^4$ is phenyl which also bears a basic substituent located at the 3- and/or 4-positions. This group of compounds possesses improved TNFα inhibitory potency in one or both of the PBMC and Human Whole Blood tests described hereinafter.

A particular group of novel compounds according to this aspect of the invention is an amide derivative of the Formula I wherein $R^1$ is amino, $C_{1-6}$alkylamino, di-($C_{1-6}$alkyl)amino, amino$C_{1-6}$alkyl, heteroaryl, heteroaryl$C_{1-6}$alkyl, heterocyclyl or heterocyclyl$C_{1-6}$alkyl;

m is 1 with the $R^1$ group located at the 3-position or m is 2 with the $R^1$ groups, which may be the same or different, located at the 3- and 4-positions;

p is 0;

$R^3$ is methyl;

q is 0; and $R^4$ is phenyl which is substituted with 1 or 2 substituents selected from amino, $C_{1-6}$alkylamino, di-($C_{1-6}$alkyl)amino, amino$C_{1-6}$alkyl, heteroaryl, heteroaryl$C_{1-6}$alkyl, heterocyclyl and heterocyclyl$C_{1-6}$alkyl, and when there is substituent it is located at the 3-position and when there are 2 substituents, which may be the same or different, they are located at the 3- and 4-positions;

or a pharmaceutically-acceptable salt thereof.

A preferred group of novel compounds according to this aspect of the invention is an amide derivative of the Formula I
wherein $R^1$ is amino, methylamino, dimethylamino, aminomethyl, pyrrolidin-1-yl, piperidino, morpholino, 4-thiamorpholino, piperazin-1-yl, 4-methylpiperazin-1-yl, 4-methylhomopiperazin-1-yl, pyrrolidin-1-ylmethyl, piperidinomethyl, 4-carbamoylpiperidin-1-ylmethyl, morpholinomethyl, 4-thiamorpholinomethyl, piperazin-1-ylmethyl, 4-methylpiperazin-1-ylmethyl, 4-ethylpiperazin-1-ylmethyl, 4-propylpiperazin-1-ylmethyl, 4-isopropylpiperazin-1-ylmethyl, 4-acetylpiperazin-1-ylmethyl or 4-methylhomopiperazin-1-ylmethyl.

m is 1 with the $R^1$ group located at the 3- or 4-position;

p is 0;

$R^3$ is methyl;

q is 0; and $R^4$ is phenyl which is substituted at the 3- or 4-position with a substituent selected from amino, methylamino, dimethylamino aminomethyl, pyrrolidin-1-yl, piperidino, morpholino, 4-thiamorpholino, piperazin-1-yl, 4-methylpiperazin-1-yl, 4-methylhomopiperazin-1-yl, pyrrolidin-1-ylmethyl, piperidinomethyl, 4-carbamoylpiperidin-1-ylmethyl, morpholinomethyl, 4-thiamorpholinomethyl, piperazin-1-ylmethyl, 4-methylpiperazin-1-ylmethyl, 4-ethylpiperazin-1-ylmethyl, 4-propylpiperazin-1-ylmethyl, 4-isopropylpiperazin-1-ylmethyl, 4-acetylpiperazin-1-ylmethyl and 4-methylhomopiperazin-1-ylmethyl;

or a pharmaceutically-acceptable salt thereof.

A more preferred group of novel compounds according to this aspect of the invention is an amide derivative of the Formula I
wherein $R^1$ is morpholino, morpholinomethyl, piperazin-1-ylmethyl or 4-methylpiperazin-1-ylmethyl;

m is 1 with the $R^1$ group located at the 3-position;

p is 0;

$R^3$ is methyl;

q is 0; and $R^4$ is phenyl which is substituted at the 3-position with a substituent selected from dimethylamino, morpholino, morpholinomethyl, piperazin-1-ylmethyl and 4-methylpiperazin-1-ylmethyl;

or a pharmaceutically-acceptable salt thereof.

Particular novel compounds of this aspect of the present invention are:

N-[2-methyl-5-(3-morpholinobenzamido)phenyl]-3-morpholinobenzamide and N-[2-methyl-5-(3-morpholinobenzamido)phenyl]-3-(4-methylpiperazin-1-yl)methylbenzamide;

and pharmaceutically-acceptable salts thereof.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric. hydrobromic, sulphuric, trifluoroacetic, citric or maleic acid; or, for example a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, el al., Journal of Pharmaceutical Sciences, 77, 285 (1988); and e) N. Kakeya, et al., Chem Pharm Bull, 32, 692 (1984).

Examples of such pro-drugs may be used to form in vivo cleavable esters of a compound of the Formula I. An in vivo cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; and $C_{1-6}$alkoxycarbonyloxyethyl esters, for example 1-methoxycarbonyloxyethyl; and may be formed at any carboxy group in the compounds of this invention.

In order to use a compound of the Formula I, or a pharmaceutically-acceptable salt or in vivo cleavable ester thereof, for the therapeutic treatment (including prophylactic treatment) of mammals including humans, it is normally formulated in accordance with standard pharmaceutical practice as a pharmaceutical composition.

According to this aspect of the invention there is provided a pharmaceutical composition which comprises an amide derivative of the Formula I, or a pharmaceutically-acceptable salt or in vivo cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 $\mu$m or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight, preferably 0.5 mg to 40 mg per kg body weight, is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis. AIDS, septic shock, ischaemic heart disease, psoriasis and the other disease states mentioned earlier in this specification.

For example, by virtue of their ability to inhibit cytokines, the compounds of the Formula I are of value in the treatment of certain inflammatory and non-inflammatory diseases which are currently treated with a cyclooxygenase-inhibitory non-steroidal anti-inflammatory drug (NSAID) such as indomethacin ketorolac, acetylsalicyclic acid. ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt or in vivo cleavable ester thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase (such as those disclosed in European Patent Applications Nos. 0351194, 0375368, 0375404, 0375452, 0375457, 0381375, 0385662, 0385663, 0385679, 0385680).

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/ or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

An amide derivative of the Formula I, or a pharmaceutically-acceptable salt or in vivo cleavable ester thereof, may be prepared by any process known to be applicable to the preparation of chemically-related compounds. Suitable processes are illustrated by, for example, those used in *J. Med. Chem.*, 1996, 39, 3343–3356. Such processes, when used to prepare a novel amide derivative of the Formula I are provided as a further feature of the invention and are illustrated by the following representative process variants in which, unless otherwise stated. $R^1$, $R^2$, $R^3$, $R^4$, m, p and q have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt or in vivo cleavable ester thereof, may be prepared by reacting a compound of the Formula III

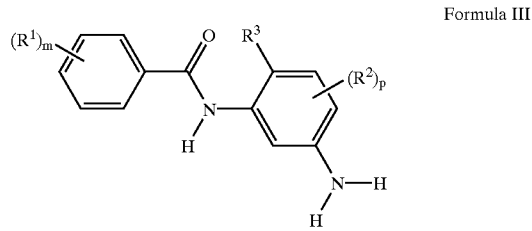

Formula III with a compound of the Formula IV

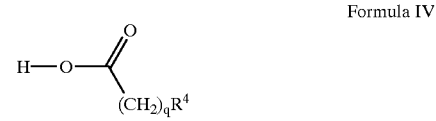

Formula IV or an activated derivative thereof, under standard amide bond forming conditions, wherein variable groups are as hereinbefore defined and wherein any functional group is protected, if necessary, and:

i. removing any protecting groups;

ii. optionally forming a pharmaceutically-acceptable salt or in vivo cleavable ester.

A suitable activated derivative of an acid of the Formula IV is, for example, an acyl halide, for example an acyl chloride formed by the reaction of the acid and an inorganic acid chloride, for example thionyl chloride: a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms).

Examples of carboxy protecting groups include straight or branched chain $C_{1-12}$alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl); and $C_{2-6}$alkenyl groups (for example allyl and vinylethyl).

Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups: lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; tri-alkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green el al., published by John Wiley & Sons for general guidance on protecting groups.

The compound of Formula III may be prepared by reduction of the corresponding nitro compound of Formula V.

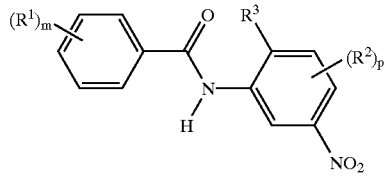

Formula V

Typical reaction conditions include the use of ammonium formate in the presence of a catalyst (for example palladium-on-carbon) in the presence of an organic solvent (preferably a polar protic solvent), preferably with heating, for example to about 60° C. Any functional groups are protected and deprotected as necessary.

The compound of Formula V may be prepared by reaction of a compound of Formula VI, or an activated derivative thereof as defined hereinbefore,

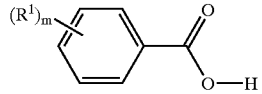

Formula VI with a compound of Formula VII under suitable amide bond forming conditions.

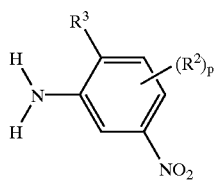

Formula VII

Typical conditions include activating the carboxy group of the compound of Formula VI for example by treatment with a halo reagent (for example oxalyl chloride) to form an acyl halide in an organic solvent at ambient temperature, then reacting the activated compound with the compound of Formula VII. Any functional, groups are protected and deprotected as necessary.

(b) A compound of the Formula I, or a pharmaceutically-acceptable salt or in vivo cleavable ester thereof, may be prepared by reacting an acid of the Formula VI

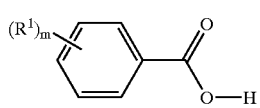

Formula VI or an activated derivative thereof as defined hereinbefore, with an aniline of the Formula VIII

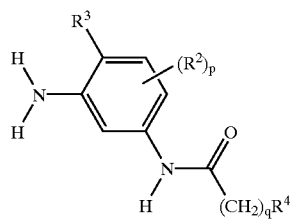

Formula VIII under standard amide bond forming conditions, wherein variable groups are as hereinbefore defined and wherein any functional group is protected, if necessary, and:
  i. removing any protecting groups;
  ii. optionally forming a pharmaceutically-acceptable salt or in vivo cleavable ester.

The aniline of Formula VIII may be prepared by reduction of the corresponding nitro compound using convention procedures as defined hereinbefore or as illustrated in the Examples.

(c) A compound of the Formula I wherein $R^1$ or a substituent on $R^4$ is heterocyclyl$C_{1-6}$alkyl may be prepared by the reaction of a compound of the Formula I wherein $R^1$ or a substituent on $R^4$ is a group of the formula -$C_{1-6}$alkyl-Z wherein Z is a displaceable group with a heterocyclyl compound.

A suitable displaceable group Z is, for example, a halogeno group such as fluoro, chloro or bromo, a $C_{1-6}$alkanesulphonyloxy group such as methanesulphonyloxy or an arylsulphonyloxy group such as 4-toluenesulphonyloxy.

The reaction is conveniently carried out in the presence of a suitable base as defined hereinbefore and in the presence of a suitable inert diluent or carrier as defined hereinbefore (d) A compound of the Formula I wherein $R^1$, $R^2$ or a substituent on $R^4$ is carboxy may be prepared by the cleavage of a compound of the Formula I wherein $R^1$, $R^2$ or a substituent on $R^4$ is $C_{1-6}$alkoxycarbonyl.

The cleavage reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10 to 150° C., preferably at or near ambient temperature.

(e) A compound of the Formula I wherein $R^1$, $R^2$ or a substituent on $R^4$ is hydroxy may be prepared by cleavage of a compound of the Formula I wherein $R^1$, $R^2$ or a substituent on $R^4$ is benzyloxy or substituted benzyloxy.

Typical reaction conditions include the hydrogenolysis of a benzyloxy group in the presence of a suitable catalyst such as palladium-on-carbon.

(f) A compound of the Formula I wherein $R^1$, $R^2$ or a substituent on $R^4$ is amino may be prepared by the reduction of a compound of the Formula I wherein $R^1$, $R^2$ or a substituent on $R^4$ is nitro.

Typical reaction conditions include the use of hydrogen or of ammonium formate in the presence of a suitable catalyst such as palladium-on-carbon.

(g) A compound of the Formula I wherein $R^1$, $R^2$ or a substituent on $R^4$ is $C_{1-6}$alkanoylamino may be prepared by the acylation of a compound of the Formula I wherein $R^1$, $R^2$ or a substituent on $R^4$ is amino.

A suitable acylating agent is, for example, any agent known in the art for the acylation of amino to acylamino, for example an acyl halide, for example a $C_{1-6}$alkanoyl chloride or bromide, conveniently in the presence of a suitable base, as defined hereinbefore, an alkanoic acid anhydride or mixed anhydride, for example a $C_{1-6}$alkanoic acid anhydride such as acetic anhydride or the mixed anhydride formed by the reaction of an alkanoic acid and a $C_{1-6}$alkoxycarbonyl halide, for example a $C_{1-6}$alkoxycarbonyl chloride, in the presence of a suitable base as defined hereinbefore. In general the acylation is carried out in a suitable inert solvent or diluent as defined hereinbefore and at a temperature, in the range, for example, −30 to 120° C., conveniently at or near ambient temperature.

The following biological assays and Examples serve to illustrate the present invention.

Biological Assays

The following assays can be used to measure the p38 kinase-inhibitory, the TNF-inhibitory and anti-arthritic effects of the compounds of the present invention:

In Vitro Enzyme Assay

The ability of compounds of the invention to inhibit the enzyme p38 kinase was assessed. Activity of particular test compounds against each of the p38α and p38β isoforms of the enzyme was determined.

Human recombinant MKK6 (GenBank Accesion Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886–2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 1265, 224–227 and Y. Jiang et al., *Journal of Biological Chemistry*, 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 μl of 10 mg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM Mg(OCOCH$_3$)$_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)] was then added followed by 'Labelled ATP' [10 μl; comprising 50 μM ATP, 0.1 μCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In Vitro Cell-based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 μg/ml streptomycin, 2 mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs (2.4×10$^5$ cells in 160 μl culture medium) were incubated with 20 μl of varying concentrations of test compound (triplicate cultures) or 20 μl culture medium containing 1% DMSO (control wells) for 30 minutes at 37° C. in a humidified (5% CO$_2$/95% air) incubator (Falcon 3072; 96 well flat-bottom tissue culture plates). 20 μl lipopolysaccharide [LPS *E.Coli* 0111:B4 (Sigma L-4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres., S., *Int. J. Immunopharmac.* (1993), 15(3), 409–413) or an inhibitor of proTNFα convertase (for example, see McGeehan, G. M. et al. *Nature* (1994) 370, 558–561). Plates were incubated for 7 hours at 37° C. (humidified incubator) after which 100 μl of the supernatant was removed from each well and stored at −70° C. (96 well round-bottom plates; Corning 25850). TNFα levels were determined in each sample using a human TNFα ELISA (see WO92/10190 and *Current Protocols in Molecular Biology*, vol 2 by Frederick M. Ausbel et al., John Wiley and Sons Inc.).

% inhibition=(LPS alone control−medium alone control)−(test concentration−medium alone control)/(LPS alone control−medium alone control)×100

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin, 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20 μl LPS (final concentration 10 μg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology*, vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex Vivo/In Vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal (i.p.) or subcutaneous (s.c.). Ninety minutes later. rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 μl of each sample was added to a set format pattern in a 96 well round bottom plate (Corning 25850). 50 μl of heparinized human blood was then added to each well, mixed and the plate was incubated for 30 min at 37° C. (humidified incubator). LPS (25 μl; final concentration 10 μg/ml) was added to the wells and incubation continued for a further 5.5 hours. Control wells were incubated with 25 μl of medium alone. Plates were then centrifuged for 10 min at 2000 rpm and 200 μl of the supernatants were transferred to a 96 well plate and frozen at −20° C. for subsequent analysis of TNF concentration by ELISA.

Data analysis by dedicated software calculates for each compound/dose:

$$\text{Percent inhibition of TNF}\alpha = \frac{\text{Mean TNF}\alpha \text{ (Controls)} - \text{Mean TNF}\alpha \text{ (Treated)} \times 100}{\text{Mean TNF}\alpha \text{ (Controls)}}$$

Alternatively, mice could be used instead of rats in the above procedure.

Test as Anti-arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.*, 146, 857.
2. Williams, R. O. et al., (1992) *Proc. Natl. Acad. Sci.*, 89, 9784.
3. Williams, R. O. et al., (1995) *Immunology*, 84, 433.
4. Badger, M. B. et al., (1996) *The Journal of Pharmacology and Experimental Therapeutics*, 279, 1453–1461.

Although the pharmacological properties of the compounds of the Formula I vary with structural change as expected, in general a compound of the Formula I gives over 30% inhibition of p38α and/or p38β at concentrations up to 10 μM and over 30% inhibition in the PBMC test at concentrations up to 50 μM. No physiologically unacceptable toxicity was observed at the effective dose for compounds tested of the present invention. By way of example:

N-[5-(2-fluoro-6-chlorobenzamido-2-methylphenyl]-4-hydroxybenzamide [Example 9, Compound No. 12] has an $IC_{50}$ of approximately 1.7 μM against p38α and an $IC_{50}$ of approximately 22 μM in the PBMC test;

N-[5-(3-aminobenzamido)-2-methylphenyl]-3,4-dimethoxybenzamide [Example 13] has an $IC_{50}$ of approximately 0.7 μM against p38α and an $IC_{50}$ of approximately 7 μM in the PBMC test;

N-[5-(3-dimethylaminobenzamido)-2-methylphenyl]-3,4-dimethoxybenzamide [Example 9, Compound No. 7] has an $IC_{50}$ of approximately 0.2 μM against p38α and an $IC_{50}$ of approximately 7 μM in the PBMC test;

N-(5-benzarmido-2-methylphenyl)-3-(4-methylpiperazin-1-yl)methylbenzamide, [Example 9, Compound No. 51] has an $IC_{50}$ of approximately 0.7 μM against p38α and an $IC_{50}$ of approximately 3 μM in the PBMC test;

N-[2-methyl-5-(3-morpholinobenzamido)phenyl]-3-morpholinobenzamide [Example 9, Compound No. 50] has an $IC_{50}$ of approximately 0.04 μM against p38α and an $IC_{50}$ of approximately 1.5 μM in the PBMC test;

N-[5-(3-cyclopentylpropionamido)-2-methylphenyl]-4-hydroxybenzamide has an $IC_{50}$ of approximately 6 μM against p38α; and N-[5-(3-cyclohexylpropionamido)-2-methylphenyl]-4-hydroxybenzamide has an $IC_{50}$ of approximately 0.4 μM against p38α and an $IC_{50}$ of approximately 7 μM in the PBMC test.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
DMF N,N-dimethylformamide
DMSO dimethylsulfoxide
MPLC medium pressure liquid chromatography
HPLC high pressure liquid chromatography

EXAMPLE 1

N-[5-(2-Bicyclo[2.2.1]hept-2-ylacetylamino)-2-methylphenyl]-4-hydroxybenzamide

A solution of N-(5-amino-2-methylphenyl)-4-hydroxybenzamide (133 mg) in dry DMF (0.5 ml) was added to 2-norbornanylacetic acid (77 mg) followed by a solution of 1-(3-dimethylaminopropyl)-3-ethylcarbodiimide hydrochloride (96 mg) in dry methylene chloride (3.0 ml). The reaction was stirred at ambient temperature for 5 hours. The solvents were removed by evaporation and the residue taken up into ethyl acetate (4.0 ml) and washed with water (3.0 ml). The aqueous layer was back extracted with ethyl acetate (4.0 ml) and the combined ethyl acetate extracts were evaporated to give 95 mg (53%) of the title product, shown to be 96% pure by HPLC.

The starting material was prepared as follows:

A) Oxalyl chloride (0.5 ml) was added slowly to a stirred suspension of 4-acetoxybenzoic acid (1.09 g), dry methylene chloride (30 ml) and DMF (one drop). The mixture was stirred for two hours at ambient temperature. A solution of 2-methyl-5-nitroaniline (760 mg) and pyridine (2.0 ml) in dry methylene chloride was added over 15 minutes. The reaction mixture was stirred for a further 2 hours, washed with 5% aqueous acetic acid (2×25 ml), water (20 ml) and 5% aqueous sodium hydrogen carbonate solution. The organic extract was dried over magnesium sulphate, filtered and evaporated to dryness. The residue was crystallised from ethyl acetate (100 ml) to give 800 mg (53%) of 4-acetoxy-N-(2-methyl-5-nitrophenyl)benzamide, melting point 207–208° C.;

NMR Spectrum: (DMSOd$_6$) 2.3 (s, 3H), 7.31 (d, 2H), 7.56 (d, 1H), 8.02 (m, 3H), 8.47 (d, 1H), 10.12 (s, 1H); Mass Spectrum: M+H$^+$ 315; Microanalysis: % Theory C 61.1, H 4.49, N 8.91; % Found C 61.0, H 4.3, N 8.8%.

B) A stirred mixture of 4-acetoxy-N-(2-methyl-5-nitrophenyl)benzamide (500 mg), ammonium formate (1.0 g) and 10% palladium on carbon (25 mg) in methanol (10 ml) was heated at 60° C. for 2 hours. The reaction mixture was cooled and filtered through diatomaceous earth (Celite®). The filtrate was evaporated to dryness and the residue triturated with water. The crude product was filtered from the aqueous solution and crystallised from methanol to give 140 mg (31% yield) of N-(5-amino-2-methylphenyl)-4-hydroxybenzamide, Melting point 277–278° C.;

NMR Spectrum: (DMSOd$_6$) 2.03 (s, 3H), 4.85 (s, 2H), 6.39 (m, 1H), 6.61 (d, 1H), 6.85 (m, 3H), 7.82 (d, 2H), 9.3 (s, 1H), 9.96 (s, 1H); Mass Spectrum: M+H$^+$ 243; Microanalysis: C$_{14}$H$_{14}$N$_2$O$_2$ requires C 69.4, H 5.8, N 11.6%; found C 69.1, H 5.8, N 11.5%.

EXAMPLE 2

N-{5-[2-(3,4-Dichlorophenyl)acetylamino]-2-methylphenyl}-4-hydroxybenzamide

The method of Example 1 was repeated using 3,4-dichlorophenylacetic acid (0.5 mmol). The reaction mixture was evaporated and the residue taken up in ethyl acetate (4 ml), washed with 1M hydrochloric acid (3.0 ml) and water (3.0 ml). The ethyl acetate extract was evaporated to give the desired product, 132 mg (68%), shown to be 92% pure by HPLC.

EXAMPLE 3

N-[5-(3-Dimethylaminobenzamido)-2-methylphenyl]-4-hydroxybenzamide

N-(5-Amino-2-methylphenyl)-4-hydroxybenzamide (85 mg) was added to a stirred solution of 3-dimethylaminobenzoic acid (89 mg) in dry DMF (0.5 ml) followed by a solution of 1-(3-dimethylaminopropyl)-3-ethylcarbodiimide hydrochloride (103 mg) in dry methylene chloride (3 ml) and 4-dimethylaminopyridine (131 mg; 1.07 mmol). The reaction was stirred at ambient temperature under argon for 18 hours. The reaction mixture was purified by MPLC on silica eluting in turn with 50%, 60% and 70% ethyl acetate in isohexane to give 17 mg (11%) of the title product; NMR Spectrum: (DMSOd$_6$) 2.17 (s, 3H), 2.96 (s, 6H), 6.80–6.95 (m, 3H), 7.15–7.35 (m, 4H), 7.58 (m, 1H), 7.79 (d, 1H), 7.87 (d, 2H), 9.62 (s, 1H), 9.95 (s, 1H), 10.10 (s, 1H); Mass Spectrum: M+H$^+$ 390; Microanalysis: % Theory C 68.6, H 5.8, N 10.3 (0.2 CH$_2$Cl$_2$), % Found C 68.1, H 5.7, N 10.9.

EXAMPLE 4

N-[5-(4-Cyanobenzamido)-2-methylphenyl]-4-hydroxybenzamide

A solution of N-(5-amino-2-methylphenyl)-4-hydroxybenzamide (121 mg) in dry DMF (1.0 ml) was added to 4-cyanobenzoic acid (88 mg), and stirred. A solution of 1-(3-dimethylaminopropyl)-3-ethylcarbodiimide hydrochloride (1 15 mg) in methylene chloride (3.0 ml) was added and the mixture stirred at ambient temperature overnight. The solvent was then evaporated and the residue treated with 5% aqueous sodium hydrogen carbonate solution (3 ml) and extracted with ethyl acetate (3×5 ml). The organic layer was washed with water (3 ml) and filtered through a silica column eluting with ethyl acetate (3×15 ml). The solvent was evaporated and the residue crystallised from ethanol/water (1:1) to give the title product (70 mg), m.p. 297–299° C.;

NMR Spectrum: (DMSOd$_6$) 2.2 (s, 3H), 6.88 (d, 2H), 7.23 (d, 1H), 7.56 (m, 1H), 7.85 (m, 3H), 8.0 (d, 2H), 8.12 (d, 2H), 9.62 (s, 1H), 10.02 (s, 1H), 10.45 (s, 1H); Mass Spectrum: M+H$^+$ 372; Microanalysis: % Theory C 70.5, H 4.6, N 11.2, % Found C 70.5, H 4.4. N 10.8.

EXAMPLE 5

N-[5-(4-Chlorobenzamido)-2-methylphenyl]-3,4-dimethoxybenzamide

Triethylamine (0.12 ml) was added to a stirred mixture of N-(5-amino-2-methylphenyl)-3,4-dimethoxybenzamide (0.1 g), 4-chlorobenzoyl chloride (0.067 ml), 4-dimethylaminopyridine (0.004 g) and methylene chloride (3 ml) and the mixture was stirred at ambient temperature for 16 hours. The reaction mixture was partitioned between methylene chloride and 2N hydrochloric acid. The organic phase was washed with a saturated aqueous solution of sodium bicarbonate and with brine dried (MgSO$_4$) and evaporated. There was thus obtained the title compound as a solid (0.086 g);

NMR Spectrum: (CDCl$_3$) 2.26 (s, 3H), 3.94 (s, 6H), 6.91 (d, 1H), 7.18 (d, 1H), 7.29–7.81 (m, 8H), 8.09 (m, 2H); Mass Spectrum: M+H$^+$ 425.

The N-[5-amino-2-methylphenyl]-3,4-dimethoxybenzamide used as starting material was prepared as follows:

A solution of 3,4-dimethoxybenzoyl chloride (11.5 g) in methylene chloride (100 ml) was added dropwise to a stirred mixture of 2-methyl-5-nitroaniline (8.74 g), pyridine (18.6 ml) and methylene chloride (200 ml) and the mixture was stirred at ambient temperature for 18 hours. The mixture was washed with 2N hydrochloric acid and with water, dried (MgSO$_4$) and evaporated. The resultant solid was dried under vacuum at 60° C. There was thus obtained N-(2-methyl-5-nitrophenyl)-3,4-dimethoxybenzamide (15.9 g), m.p.>300° C.;

NMR Spectrum: (CDCl$_3$) 2.43 (s, 3H), 3.94 (m, 6H), 6.93 (m, 1H), 7.38 (m, 2H), 7.51 (m, 1H), 7.75 (br s, 1H), 7.94 (d, 1H), 8.89 (br m, 1H).

10% Palladium-on-carbon (4 g) was added to a stirred suspension of the material so obtained in methanol (1500 ml) and the mixture was stirred under an atmosphere of hydrogen gas. After cessation of hydrogen uptake, the catalyst was removed by filtration and the filtrate was evaporated. The residue was washed with diethyl ether and dried under vacuum at 60° C. There was thus obtained the required starting material (11.3 g), m.p. 157–158° C.;

NMR Spectrum: (CDCl$_3$) 2.24 (s, 3H), 3.64 (br s, 2H), 3.95 (m, 6H), 6.44 (m, 1H), 6.93 (d, 1H), 6.98 (d, 1H), 7.38 (m, 1H), 7.54 (m, 2H), 7.6 (br s, 1H).

EXAMPLE 6

N-[5-(3-Bromobenzamido)-2-methylphenyl]-3,4-dimethoxybenzamide

3-Bromobenzoyl chloride (1.53 g) was added to a stirred mixture of N-(5-amino-2-methylphenyl)-3,4-dimethoxybenzamide (2 g), pyridine (1.7 ml) and methylene chloride (40 ml) and the mixture was stirred at ambient temperature for 18 hours. The precipitated solid was isolated, washed with diethyl ether and dried under vacuum at 60° C. There was thus obtained the title compound (1.89 g); m.p. 136–138° C.;

NMR Spectrum: (DMSOd$_6$) 2.18 (s, 3H), 3.81 (s, 6H), 7.05 (d, 1H), 7.23 (d, 1H), 7.45 (t, 1H), 7.56 (m, 2H), 7.63 (m, 1H), 7.78 (m, 2H), 7.95 (d, 1H), 8.13 (d, 1H), 9.75 (br s, 1H), 10.31 (br s, 1H); Mass Spectrum: M+H$^+$ 469; Elemental Analysis: Found: C, 59.1; H, 4.4; N, 5.9; C$_{23}$H$_{21}$N$_2$O$_4$Br requires C, 58.9; H, 4.5; N, 6.0%.

EXAMPLE 7

N-[5-Benzamido-2-methylphenyl]-3,4-dimethoxybenzamide 3,4-Dimethoxybenzoyl chloride (0.3 g) was added to a stirred mixture of N-(3-amino-4-methylphenyl)benzamide (0.23 g), triethylamine (0.4 ml) and methylene chloride (10 ml) and the mixture was stirred at ambient temperature for 16 hours. The precipitate was isolated, washed with water and with diethyl ether, dried under vacuum at 40° C. There was thus obtained the title compound (0.319 g);

NMR Spectrum: (DMSOd$_6$) 2.18 (s, 3H), 3.82 (s, 6H), 7.06 (d, 1H), 7.25 (d, 1H), 7.55 (m, 6H), 7.82 (s, 1H), 7.94 (d, 2H), 9.76(s, 1H), 10.20 (s, 1H); Mass Spectrum: M+H 391.

The N-(3-amino-4-methylphenyl)benzamide used as a starting material was prepared as follows:

Benzoyl chloride (1.9 ml) was added to a stirred mixture of 2,4-diaminotoluene (2 g), triethylamine (5.57 ml) and methylene chloride (80 ml) and the mixture was stirred at ambient temperature for 16 hours. The mixture was washed with a saturated aqueous solution of sodium bicarbonate. The organic phase was dried (MgSO$_4$) and evaporated. The residue was triturated with a mixture of ethyl acetate and diethyl ether. There was thus obtained the required starting material (1.32 g); NMR Spectrum: (DMSOd$_6$) 2.01 (s, 3H), 4.8 (s, 2H), 6.82 (m 2H), 7.11 (s, 1H), 7.5 (m, 3H), 7.91 (mn, 2H), 9.86 (s, 1H); Mass Spectrum: M+H$^+$ 227.

EXAMPLE 8

N-[5-(3,4-Dimethoxybenzamido)-2-methylphenyl]-3-dimethylaminobenzamide

Oxalyl chloride (1.14 g) was added to a stirred mixture of 3-dimethylaminobenzoic acid (1.23 g), DMF (1 drop) and methylene chloride (40 ml) and the mixture was stirred at ambient temperature for 3 hours. The solvent was evaporated and the residue was dissolved in methylene chloride (40 ml). The resultant solution was added dropwise to a stirred mixture of N-(3-amino-4-methylphenyl)-3,4-dimethoxybenzamide (1.78 g), pyridine (3.77 ml) and methylene chloride (20 ml) and the mixture was stirred at ambient temperature for 48 hours. The reaction mixture was washed in turn with water, a saturated aqueous sodium bicarbonate solution, brine and water. The organic solution was dried (MgSO$_4$) and evaporated. The solid so obtained was recrystallised from ethyl acetate and dried under vacuum at 60° C. There was thus obtained the title compound (0.359 g), m.p. 204–205° C.;

NMR Spectrum: (DMSOd$_6$) 2.28 (s, 3H), 3.01 (s, 6H), 3.93 (d, 6H), 6.88 (m, 2H), 7.09 (d, 1H), 7.18 (d, 1H), 7.26 (s, 1H), 7.33 (t, 1H), 7.41 (m, 1H); 7.5 (d, H), 7.76 (m, 2H), 8.05 (br s, 1H), 8.13 (d, 1H); Mass Spectrum: M+H$^+$ 434.

The N-(3-amino-4-methylphenyl)-3,4-dimethoxybenzamide used as starting material was prepared as follows:

A solution of 3,4-dimethoxybenzoyl chloride (13.2 g) in methylene chloride (200 ml) was added dropwise to a stirred mixture of 4-methyl-3-nitroaniline (10 g), pyridine (21.3 ml), 4-dimethylaminopyridine (0.4 g) and methylene chloride (100 ml) and the resultant solution was stirred at ambient temperature for 18 hours. The reaction mixture was washed with 2N hydrochloric acid and water dried (MgSO$_4$) and evaporated. The residue was triturated under diethyl ether and the resultant solid was dried under vacuum at 60° C. There was thus obtained N-(4-methyl-3-nitrophenyl)-3,4-dimethoxybenzamide (18.1 g), m.p. 148–149° C.;

NMR Spectrum: (CDCl$_3$) 2.58 (s, 3H), 3.96 (s, 6H), 6.92 (d, 1H), 7.33 (d, 1H), 7.43 (m, 1H), 7.51 (d, 1H), 7.9 (m, 1H), 7.97 (br s, 1H), 8.24 (d, 1H).

Ammonium format (33.9 g) was added to a stirred suspension of N-(4-methyl-3-nitrophenyl)-3,4-dimethoxybenzamide (17 g) and 10% palladium-on-carbon (4 g) in ethanol (650 ml) and the mixture was stirred and heated to reflux for 1.5 hours. The reaction mixture was allowed to cool to ambient temperature and filtered. The filtrate was evaporated and the residue was partitioned between methylene chloride and a saturated aqueous sodium bicarbonate solution. The organic phase was washed with water, dried (MgSO$_4$) and evaporated. The residue was triturated under diethyl ether and the resultant solid was dried under vacuum at 60° C. There was thus obtained the required starting material (12.6 g), m.p. 143–144° C.; NMR Spectrum: (CDCl$_3$) 2.13 (s, 3H), 3.65 (br s, 2H), 3.93 (s, 6H), 6.73 (m, 1H), 6.93 (d, 1H), 6.87 (m, 1H), 7.0 (m, 1H), 7.28 (d, 1H), 7.36 (m, 1H), 7.48 (d, 1H), 7.7 (br s, 1H).

EXAMPLE 9

Using an analogous procedure to that described in Example 3, 5, 6 or 7, the appropriate benzoyl chloride was reacted with the appropriate aniline to give the compounds described in Table I. With reference to the chemical formula immediately hereinafter in Table I and when an analogous procedure to that described in Example 3, 5 or 6 is employed, the appropriate benzoyl chloride is of the formula R—C$_6$H$_4$—COCl and when an analogous procedure to that described in Example 7 is employed, the appropriate benzoyl chloride is of the formula (R$^1$)$_m$—C$_6$H$_{(5-m)}$—COCl

TABLE I

| No. | (R$^1$)$_m$ | R | Method | Note |
|---|---|---|---|---|
| 1 | 3,4-dimethoxy | 4-bromo | Ex. 6 | a |
| 2 | 3,4-dimethoxy | 4-fluoro | Ex. 6 | b |
| 3 | 3,4-dimethoxy | 3-benzyloxy | Ex. 6 | c |
| 4 | 3,4-dimethoxy | 4-benzyloxy | Ex. 6 | d |
| 5 | 3,4-dimethoxy | 3-nitro | Ex. 6 | e |
| 6 | 3,4-dimethoxy | 4-cyano | Ex. 5 | f |
| 7 | 3,4-dimethoxy | 3-dimethylamino | Ex. 7 | g |
| 8 | 3,4-dimethoxy | 4-morpholino | Ex. 6 | h |
| 9 | 3,4-dimethoxy | 4-(4-thiamorpholino) | Ex. 6 | i |
| 10 | 3,4-dimethoxy | 3,4-dimethoxy | Ex. 5 | j |
| 11 | 4-hydroxy | hydrogen | Ex. 3 | k |
| 12 | 4-hydroxy | 2-fluoro-6-chloro | Ex. 3 | l |
| 13 | 4-hydroxy | 4-benzyloxy | Ex. 3 | m |
| 14 | 4-hydroxy | 3,5-dimethoxy | Ex. 3 | n |
| 15 | 4-hydroxy | 4-phenyl | Ex. 3 | o |
| 16 | 4-hydroxy | 4-nitro | Ex. 3 | p |
| 17 | 4-acetoxy | 4-cyano | Ex. 7 | q |
| 18 | 4-propyl | 3-dimethylamino | Ex. 7 | r |
| 19 | 4-ethyl | 3-dimethylamino | Ex. 7 | s |
| 20 | 4-tert-butyl | 3-dimethylamino | Ex. 7 | t |
| 21 | 4-butyl | 3-dimethylamino | Ex. 7 | u |
| 22 | 3,4-dimethyl | 3-dimethylamino | Ex. 7 | v |
| 23 | 2-methoxy | 3-dimethylamino | Ex. 7 | w |
| 24 | 3-methoxy | 3-dimethylamino | Ex. 7 | x |
| 25 | 4-methoxy | 3-dimethylamino | Ex. 7 | y |
| 26 | 3-ethoxy | 3-dimethylamino | Ex. 7 | z |
| 27 | 4-ethoxy | 3-dimethylamino | Bx. 7 | aa |
| 28 | 4-isopropoxy | 3-dimethylamino | Ex. 7 | bb |
| 29 | 3-butoxy | 3-dimethylamino | Ex. 7 | cc |
| 30 | 2,4-dimethoxy | 3-dimethylamino | Ex. 7 | dd |
| 31 | 3,4-diethoxy | 3-dimethylamino | Ex. 7 | ee |
| 32 | 3,4,5-trimethoxy | 3-dimethylamino | Ex. 7 | ff |
| 33 | 3-chloro | 3-dimethylamino | Ex. 7 | gg |
| 34 | 4-chloro | 3-dimethylamino | Ex. 7 | hh |
| 35 | 2-fluoro | 3-dimethylamino | Ex. 7 | ii |
| 36 | 3,5-difluoro | 3-dimethylamino | Ex. 7 | jj |
| 37 | 3-trifluoromethyl | 3-dimethylamino | Ex. 7 | kk |
| 38 | 4-trifluoromethyl | 3-dimethylamino | Ex. 7 | ll |
| 39 | 3-cyano | 3-dimethylamino | Ex. 7 | mm |
| 40 | 4-cyano | 3-dimethylamino | Ex. 7 | nn |
| 41 | 4-methoxycarbonyl | 3-dimethylamino | Ex. 7 | oo |
| 42 | 4-cyano | 4-cyano | Ex. 5 | pp |
| 43 | hydrogen | hydrogen | Ex. 7 | qq |
| 44 | 3,4,5-trimethoxy | 4-cyano | Ex. 7 | rr |
| 45 | 3,4,5-trimethoxy | hydrogen | Ex. 7 | ss |
| 46 | 3,4,5-trimethoxy | 3-trifluoromethyl | Ex. 7 | tt |
| 47 | 3,4,5-trimethoxy | 3-morpholino | Ex. 6 | uu |
| 48 | 3-bromo | 3-dimethylamino | Ex. 6 | vv |
| 49 | 3-nitro | 3-dimethylamino | Ex. 6 | ww |
| 50 | 3-morpholino | 3-morpholino | Ex. 6 | xx |
| 51 | 3-(4-methylpiperazin-1-yl)methyl | hydrogen | Ex. 5 | yy |
| 52 | 3-(4-methylpiperazin-1-yl)methyl | 3-trifluoromethyl | Ex. 5 | zz |
| 53 | 3-(4-methylpiperazin-1-yl)methyl | 2-fluoro | Ex. 5 | aaa |
| 54 | 3-(4-methylpiperazin-1-yl)methyl | 4-fluoro | Ex. 5 | bbb |
| 55 | 3-(4-methylpiperazin-1-yl)methyl | 2-chloro | Ex. 5 | ccc |
| 56 | 3-(4-methylpiperazin-1-yl)methyl | 3-chloro | Ex. 5 | ddd |
| 57 | 3-(4-methylpiperazin-1-yl)methyl | 4-chloro | Ex. 6 | eee |
| 58 | 3-(4-methylpiperazin-1-yl)methyl | 2,5-difluoro | Ex. 6 | fff |
| 59 | 3-(4-methylpiperazin-1-yl)methyl | 3,5-difluoro | Ex. 5 | ggg |

TABLE I-continued

| No. | (R¹)ₘ | R | Method | Note |
|---|---|---|---|---|
| 60 | 3-(4-methylpiperazin-1-yl)methyl | 2,4-dichloro | Ex. 5 | hhh |
| 61 | 3-(4-methylpiperazin-1-yl)methyl | 3,4-dichloro | Ex. 5 | iii |
| 62 | 3-(4-methylpiperazin-1-yl)methyl | 2-methoxy | Ex. 6 | jjj |
| 63 | 3-(4-methylpiperazin-1-yl)methyl | 4-methoxy | Ex. 5 | kkk |
| 64 | 3-(4-methylpiperazin-1-yl)methyl | 3-ethoxy | Ex. 5 | lll |
| 65 | 3-(4-methylpiperazin-1-yl)methyl | 3,4-dimethoxy | Ex. 5 | mmm |
| 66 | 3-(4-methylpiperazin-1-yl)methyl | 3-cyano | Ex. 5 | nnn |
| 67 | 3-(4-methylpiperazin-1-yl)methyl | 4-methoxycarbonyl | Ex. 5 | ooo |
| 68 | 3-(4-methylpiperazin-1-yl)methyl | 3-morpholino | Ex. 5 | ppp |

Notes a) The reactants were 4-bromobenzoyl chloride and N-(5-amino-2-methylphenyl)-3,4-dimethoxybenzamide. The product gave the following data: m.p. 221–222° C.; NMR (DMSOd₆) 2.18 (s, 3H), 3.83 (s, 6H), 7.06 (d, 1H), 7.23 (d, 1H), 7.54 (m, 2H), 7.63 (m, 1H), 7.72 (d, 2H), 7.8 (d, 1H), 7.9 (d, 2H), 9.75 (s, 1H), 10.28 (br s, 1H); Mass M+H 469.

b) The product gave the following data: m.p. 210–211° C.; NMR (DMSOd₆) 2.18 (s, 3H), 3.83 (s, 6H), 7.07 (d, 1H), 7.23 (d, 1H), 7.35 (t, 2H), 7.55 (m, 2H), 7.57 (d, 1H), 7.63 (m, 1H), 7.8 (d, 1H), 8.03 (m, 2H), 9.75 (br s, 1H), 10.39 (br s, 1H); Mass M+H 409.

c) The product gave the following data : m.p. 208–209° C.; NMR (DMSOd₆) 2.21 (s, 3H), 3.83 (s, 6H), 5.18 (s, 2H), 7.06 (d, 1H), 7.21 (m, 2H), 7.4 (m, 5H), 7.55 (m, 3H), 7.62 (m, 1H), 7.8 (d, 1H), 9.77 (br s, 1H), 10.17 (br s, 1H); Mass M+H 497.

d) The product gave the following data: m.p. 186–187° C.; NMR (DMSOd₆) 2.17 (s, 3H), 3.83 (s, 6H), 5.18 (s, 2H), 7.07 (d, 1H), 7.13 (d, 2H), 7.2 (d, 1H), 7.37 (m, 3H), 7.45 (m, 2H), 7.55 (m, 2H), 7.63 (m, 1H), 7.8 (d, 1H), 7.94 (d, 2H), 9.74 (br s, 1H), (br s, 1H); Mass M+H 497.

e) The product gave the following data: m.p. 232–233° C.; NMR (DMSOd₆) 2.19 (s, 3H), 3.83 (s, 6H), 7.07 (d, 1H), 7.24 (d, 1H), 7.61 (m, 3H), 7.83 (t, 2H), 8.45 (m, 2H), 8.79 (d, 1H), 9.76 (s, 1H), 10.55 (br s, 1H); Mass M–H 434.

f) The reactants were 4-cyanobenzoyl chloride and N-(5-amino-2-methylphenyl)-3,4-dimethoxybenzamide. The product gave the following data: NMR (CDCl₃) 2.23 (s, 3H), 3.95 (m, 6H), 6.69–8.45 (m, 12H); Mass M+H 416.

g) The reactants were 3,4-dimethoxybenzoyl chloride and N-(3-amino-4-methylphenyl)-3-dimethylaminobenzamide. The product gave the following data: NMR (DMSOd₆) 2.18 (s, 3H), 2.94 (s, 6H), 3.82 (s, 6H), 6.88 (d, 1H), 7.05 (d, 1H), 7.20 (m, 3H), 7.28 (m, 1H), 7.58 (m, 2H), 7.63 (d, 1H), 7.78 (s, 1H), 9.76 (s, 1H), 10.08 (s, 1H); Mass M+H 434.

The N-(3-amino-4-methylphenyl)-3-dimethylaminobenzamide used as starting material was prepared as follows:

Oxalyl chloride (13.0 ml) was added dropwise to a stirred mixture of 3-dimethylaminobenzoic acid (20.3 g) and DMF (a few drops) which had been cooled to 0° C. The mixture was allowed to warm to ambient temperature and was stirred for 4 hours. The resultant mixture was evaporated and the residue was dissolved in methylene chloride (150 ml), 4-Methyl-3-nitroaniline (15.2 g) and triethylamine (27.9 ml) were added in turn and the resultant mixture was stirred at ambient temperature for 16 hours. The reaction mixture was washed in turn with water, with a saturated solution of sodium bicarbonate and with brine, dried (MgSO₄) and evaporated. The residue was triturated under a mixture of ethyl acetate and isohexane. The solid so obtained was filtered off and recrystallised from ethanol to give N-(3-nitro-4-methylphenyl)-3-dimethylaminobenzamide (6.1 g); NMR (DMSOd₆) 2.46 (s, 3H), 2.95 (s, 6H), 6.92 (d, 1H), 7.22 (m, 2H), 7.32 (t, 1H), 7.45 (d, 1H), 7.97 (d, 1H), 8.53 (s, 1H), 10.43 (s, 1H); Mass M+H⁺ 300;

After repetition of the previous reactions, a sample (8.25 g) was added to a stirred suspension of ammonium formate (17.4 g), and 10% palladium-on-carbon (1 g) in methanol (250 ml). The mixture was stirred and heated to reflux for 4 hours. The mixture was allowed to cool and then filtered. The filtrate was evaporated and water was added to the residue. The resultant solid was isolated and washed in turn with water, with ethyl acetate and with diethyl ether. The solid was dried in a vacuum oven at 40° C. to give N-(3-amino-4-methylphenyl)-3-dimethylaminobenzamide (6.89 g);

NMR (DMSOd₆) 2.0 (s, 3H), 2.94 (s, 6H), 4.78 (s, 2H), 6.82 (m, 3H), 7.07 (s, 1H), 7.17 (m, 2H), 7.25 (m, 1H), 9.74 (s, 1H); Mass M+H⁺ 270.

h) The reactants were 4-morpholinobenzoyl chloride and N-(5-amino-2-methylphenyl)-3,4-dimethoxybenzamide. The product gave the following data: m.p. 226–228° C.; NMR (DMSOd₆) 2.18 (s, 3H), 3.23 (t, 4H) 3.76 (t, 4H), 3.82 (s, 6H), 7.01 (d, 2H), 7.08 (d, 1H), 7.19 (d, 1H), 7.56 (m, 2H), 7.62 (d, 1H), 7.79 (s, 1H), 7.88 (d, 2H), 9.75 (s, 1H), 9.95 (s, 1H); Mass M+H 476.

The 4-morpholinobenzoyl chloride used as a starting material was prepared as follows:

Morpholine (2.16 g) was added to a stirred mixture of benzyl 4-fluorobenzoate (3.1 g), potassium carbonate (4.48 g) and DMSO (45 ml) and the reaction mixture was heated to 100° C. for 36 hours. The mixture was cooled to ambient temperature and partitioned between diethyl ether and water. The organic phase was washed with brine, dried (MgSO₄) and evaporated. The residue was recrystallised from a 3:1 mixture of hexane and ethyl acetate to give benzyl 4-morpholinobenzoate (2.24 g) as a colourless solid, m.p. 85–86° C.; NMR Spectrum: (CDCl₃) 3.19 (t, 4H), 3.77 (t, 4H), 5.23 (s, 2H), 6.78 (d, 2H), 7.30 (m, 5H), 7.9 (d, 2H).

Palladium-on-carbon catalyst (0.12 g) was added to a stirred solution of the above benzyl ester (1.50 g) in a mixture of ethanol (100 ml) and ethyl acetate (15 ml). The mixture was stirred under an atmosphere of hydrogen. After cessation of hydrogen uptake, the catalyst was removed by filtration and the filter cake was washed with ethanol. The combined filtrates were evaporated to give 4-morpholinobenzoic acid (0.69 g); NMR Spectrum: (DMSOd$_6$) 3.22 (t, 4H), 3.72 (t, 4H), 6.96 (d, 2H), 7.78 (d, 2H).

Oxalyl chloride (0.062 ml) was added dropwise to a stirred suspension of 4-morpholinobenzoic acid (0.113 g) in methylene chloride (5 ml) which had been cooled to 0° C. DMF (1 drop) was added and the mixture was stirred at ambient temperature for 4 hours. The solvent was evaporated to give 4-morpholinobenzoyl chloride which was used without further purification.

i) The product gave the following data: m.p. 236–238° C.; NMR (DMSOd$_6$) 2.18 (s, 3H), 2.61 (t, 4H), 3.72 (t, 4H), 3.82 (s, 6H), 6.95 (d, 2H), 7.06 (d, 1H), 7.18 (d, 1H), 7.56 (m, 2H), 7.62 (d, 1H), 7.8 (s, 1H), 7.82 (d, 2H), 9.75 (s, 1H), 9.9 (s, 1H); Mass M+H 492.

The 4-(4-thiamorpholino)benzoyl chloride used as a starting material was prepared as follows:

Ethyl 4-(4-thiamorpholino)benzoate was prepared from ethyl 4-fluorobenzoate and thiamorpholine using an analogous procedure to that described in Note h) for the preparation of benzyl 4-morpholinobenzoate. The material so obtained had m.p. 46.5–47.5° C. and NMR (CDCl$_3$) 1.3 (t, 3H), 2.62 (t, 4H), 3.63 (t, 4H), 4.23 (m, 2H), 6.78 (d, 2H), 7.82 (d, 2H).

Ethyl 4-(4-thiamorpholino)benzoate (1.02 g) was added to a solution of sodium hydroxide (0.32 g) in 90% ethanol (10 ml) and the solution was stirred at ambient temperature for 18 hours. The ethanol was evaporated and 1N hydrochloric acid (8 ml) was added to the residue. The mixture was stirred for 1 hour. The precipitate was isolated and washed with water. The material was triturated under ethyl acetate to give 4-(4-thiamorpholino)benzoic acid (0.66 g) as a colourless solid, m.p. 238–240° C.;

NMR (DMSOd) 2.6 (t, 4H), 3.73 (t, 4H), 6.91 (d, 2H), 7.75 (d, 2H), 12.2 (s, 1H).

The acid so obtained was converted into the required benzoyl chloride using an analogous procedure to that described in Note h).

j) The reactants were 3,4-dimethoxybenzoyl chloride and 2,4-diaminotoluene. The product gave the following data: NMR (DMSOd$_6$) 2.18 (s, 3H), 3.82 (s, 12H), 7.06 (d, 2H), 7.21 (d, 1H), 7.57 (m, 5H), 7.76 (s, 1H), 9.74 (s, 1H), 10.0 (s, 1H); M+H 451.

k) The reactants were benzoyl chloride and N-(5-amino-2-methylphenyl)-4-hydroxybenzamide. The product gave the following data: NMR (DMSOd$_6$) 2.2 (s, 3H), 6.87 (d, 2H), 7.21 (d, 1H), 7.56 (m, 4H), 7.9 (m, 5H), 9.6 (s, 1H), 10.0 (s, 1H), 10.2 (s, 1H); Mass M+H 347.

l) The product gave the following data: Mass M+H 399.

m) The product gave the following data: NMR (DMSOd$_6$) 2.19 (s, 3H), 5.2 (s, 2H), 6.68 (d, 2H), 7.15 (m, 3H), 7.4 (m, 5H), 7.58 (m, 1H), 7.8 (d, 1H), 7.88 (d, 2H), 7.95 (d, 2H), 9.6 (s, 1H), 10.02 (s, 1H), 10.05 (s, 1H); Mass M+H 453.

n) The product gave the following data: Mass M+H 407.

o) The product gave the following data: NMR (DMSOd$_6$) 2.21 (s, 3H), 6.87 (d, 2H), 7.22 (d, 1H), 7.48 (m, 4H), 7.61 (m, 1H), 7.8 (m, 6H), 8.08 (d, 2H), 9.63 (s, 1H), 10.05 (s, 1H) 10.25 (s, 1H); Mass M+H 423.

p) The product gave the following data: NMR (DMSOd$_6$) 2.18 (s, 3H), 3.68 (s, 2H), 6.86 (d, 2H), 7.17 (d, 1H), 7.35 (m, 2H), 7.6 (m, 3H), 7.86 (d, 2H), 9.54 (s, 1H (s, 1H), 10.12 (s, 1H); Mass M+H 406.

q) The reactants were 4-acetoxybenzoyl chloride and N-(3-amino-4-methylphenyl)-4-cyanobenzamide, 4-Dimethylaminopyridine (0.15 equivalents) was added to catalyse the reaction. The product gave the following data: NMR (DMSOd$_6$) 2.18 (s, 3H), 2.26 (s, 3H), 7.25 (m, 3H), 7.57 (d, 1H), 7.84 (s, 1H), 8.0 (m, 4H), 8.11 (d, 2H), 9.91 (s, 1H), 10.46 (s, 1H); Mass: (M–H) 412.

The N-(3-amino-4-methylphenyl)-4-cyanobenzamide used as starting material was prepared as follows:

Triethylamine (23 ml) was added to a suspension of 3-nitro-4-methylaniline (0.8 g), 4-cyanobenzoyl chloride (13.1 g), 4-dimethylaminopyridine (0.8 g) in methylene chloride (200 ml) which had been cooled to 0° C. The reaction mixture was allowed to warm to ambient temperature and was stirred for 5 hours. The mixture was partitioned between methylene chloride 0.5N hydrochloric acid solution. The organic phase was dried (MgSO$_4$) and evaporated and the residue was triturated under isohexane. The solid was isolated and dried under vacuum at 55° C. There was thus obtained (3-nitro-4-methylphenyl)-4-cyanobenzamide (18.3 g); NMR (DMSOd$_6$) 2.5 (s, 3H), 7.49 (d, 1H), 7.96 (m, 1H), 8.05 (d, 2H), 8.12 (d, 2H), 8.51 (d, 1H), 10.77 (s, 1H).

A solution of tin(II) chloride dihydrate (15.4 g) in concentrated hydrochloric acid (80 ml) was added to a suspension of N-(3-nitro-4-methylphenyl)-4-cyanobenzamide (6.39 g) in acetic acid (120 ml). The mixture was stirred and heated to reflux for 2 hours. The mixture was allowed to cool to ambient temperature and was basified by the addition of 2N sodium hydroxide solution. The precipitated solid was isolated and dried under vacuum at 55° C. to give N-(3-amino-4-methylphenyl)-4-cyanobenzamide (5.62 g); NMR (DMSOd$_6$) 2.01 (s, 3H), 4.85 (s, 2H), 6.80 (d, 1H), 6.86 (d, 1H), 7.11 (s, 1H), 7.96 (d, 2H), 8.06 (d, 2H), 10.11 (s, 1H).

r) The reactants were 4-propylbenzoyl chloride and N-(3-amino-4-methylphenyl)-3-dimethylaminobenzamide. The product gave the following data: NMR (DMSOd$_6$) 0.89 (m, 3H), 1.61 (m, 2H), 2.19 (s, 3H), 2.62 (m, 2H), 2.95 (s, 6H), 6.89 (d, 1H), 7.22 (m, 3H), 7.30 (m, 3H), 7.57 (m, 1H), 7.78 (m, 1H), 7.9 (m, 2H), 9.8 (s, 1H), 10.08 (s, 1H); Mass M+H 416.

s) The product gave the following data: Mass M+H 402.

t) The product gave the following data: NMR (DMSOd$_6$) 2.18 (s, 3H), 2.94 (s, 6H), 6.9 (d, 1H), 7.20 (m, 3H), 7.28 (t, 1H), 7.55 (m, 3H), 7.8 (s, 1H), 7.91 (d, 2H), 9.79 (s, 1H), 10.08 (s, 1H); Mass M+H 430.

u) The product gave the following data: Mass M+H 430.

v) The product gave the following data: Mass M+H 402.

w) The product gave the following data: NMR (DMSOd$_6$) 2.28 (s, 3H), 2.95 (s, 6H), 3.99 (s, 3H), 6.9 (m, 1H), 7.11 (m, 1H), 7.25 (m, 5H), 7.55 (m, 2H), 7.9 (d, 1H), 8.33 (s, 1H), 9.81 (s, 1H), 10.09 (s, 1H); Mass M+H 404.

x) The product gave the following data: NMR (DMSOd$_6$) 2.29 (s, 3H), 3.0 (s, 6H), 3.87 (s, 3H), 6.86 (m, 1H), 7.1 (m, 2H), 7.2 (d, 1H), 7.28 (m, 2H), 7.4 (m, 2H), 7.45 (br s, 1H), 7.72 (m, 1H), 7.77 (br s, 1H), 7.98 (br s, 1H), 8.08 (d, 1H); Mass M+H 404.

y) The product gave the following data: NMR (DMSOd$_6$) 2.18 (s, 3H), 2.94 (s, 6H), 3.82 (s, 3H), 6.89 (d, 1H), 7.04 (d, 2H), 7.2 (m, 3H), 7.29 (td, 1H), 7.56 (d, 1H), 7.78 (s, 1H), 7.95 (d, 2H), 9.72 (s, 1H), 10.07 (s, 1H); Mass M+H 404.

z) The product gave the following data: Mass M+H 418.

aa) The product gave the following data: Mass M+H 418.

bb) The product gave the following data: NMR (DMSOd$_6$) 1.28 (d, 6H), 2.18 (s, 3H), 2.95 (s, 6H), 4.72 (m, 1H), 6.89 (d, 1H), 7.01 (d, 2H), 7.19 (m, 3H), 7.27 (m, 1H), 7.56 (d, 1H), 7.78 (s, 1H), 7.93 (d, 2H), 9.7 (s, 1H), 10.08 (s, 1H); Mass M+H 432.

cc) The product gave the following data: NMR (DMSOd$_6$) 0.93 (t, 3H), 1.44 (m, 2H), 2.71 (m, 2H), 2.18 (s, 3H), 2.94

(s, 6H), 4.04 (t, 2H), 6.9 (d, 1H), 7.03 (d, 2H), 7.26 (m, 4H), 7.56 (d, 1H), 7.8 (s, 1H), 7.94 (d, 2H), 9.71 (s, 1H), 10.08 (s, 1H); Mass M+H 446.

dd) The product gave the following data: NMR (DMSOd$_6$) 2.27 (s, 3H), 2.95 (s, 6H), 3.85 (s, 3H), 4.05 (s, 3H), 6.72 (m, 2H), 6.89 (d, 1H), 7.22 (m, 4H), 7.51 (d, 1H), 7.95 (d, 1H), 8.42 (d, 1H), 9.72 (s, 1H), 10.01 (s, 1H); Mass M+H 434.

ee) The product gave the following data: Mass M+H 462. The 3,4-diethoxybenzoyl chloride used as a starting material was prepared by the reaction of 3,4-diethoxybenzoic acid and oxalyl chloride.

ff) The product gave the following data: NMR (DMSOd$_6$) 2.18 (s, 3H) 2.94 (s, 6H), 3.72 (s, 3H), 3.84 (s, 6H), 6.89 (d, 1H), 7.25 (m, 6H), 7.56 (d, 1H), 7.77 (s, 1H), 9.86 (s, 1H), 10.09 (s, 1H); Mass M+H 464.

gg) The product gave the following data: Mass M+H 408.

hh) The product gave the following data: Mass M+H 408.

ii) The product gave the following data: NMR (DMSOd$_6$) 2.22 (s, 3H), 2.95 (s, 6H), 6.9 (d, 1H), 7.26 (m, 6H), 7.56 (m, 2H), 7.71 (t, 1H), 7.92 (s, 1H), 9.82 (s, 1H), 10.1 (s, 1H); Mass M+H 392.

jj) The product gave the following data: NMR (DMSOd$_6$) 2.18 (s, 3H), 2.95 (s, 6H), 6.89 (d, 1H), 7.25 (m, 4H), 7.55 (m, 2H), 7.63 (m, 2H), 7.79 (s, 1H), 10.06 (s, 1H), 10.1 (s, 1H); Mass M+H 410.

kk) The product gave the following data: NMR (DMSOd$_6$) 2.19 (s, 3H) 2.95 (s, 6H) 6.9 (d, 1H), 7.24 (m, 4H), 7.58 (d, 1H) 7.78 (m, 2H), 7.96 (d, 1H), 8.28 (d, 2H) 10.11 (s, 1H), 10.19 (s, 1H); Mass M+H 442.

ll) The product gave the following data: Mass M+H 442.

mm) The product gave the following data: NMR (DMSOd$_6$) 2.19 (s, 3H), 2.95 (s, 6H), 6.89 (d, 1H), 7.24 (m, 4H), 7.58 (d, 1H), 7.75 (t, 1H), 7.81 (s, 1H), 8.06 (d, 1H), 8.23 (d, 1H), 8.4 (s, 1H), 10.11 (s, 2H); Mass M+H 399.

nn) The product gave the following data: Mass M+H 399.

oo) The product gave the following data: NMR (DMSOd$_6$) 2.19 (s, 3H), 2.95 (s, 6H), 3.89 (s, 3H), 6.89 (d, 1H), 7.25 (m, 4H), 7.57 (d, 1H), 7.8 (s 1H), 8.08 (s, 4H), 9.8 (s, 1H), 10.1 (s, 1H); Mass M+H 432.

pp) The reactants were 4-cyanobenzoyl chloride and 2,4-diaminotoluene. The product gave the following data: NMR (DMSOd$_6$) 2.02 (s, 3H), 7.44 (d, 1H), 7.59 (d, 1H), 7.84 (d, 1H), 8.0 (m, 4H), 8.1 (m, 4H), 10.16 (s, 1H), 10.48 (s, 1H); Mass M+H 381.

qq) The reactants were benzoyl chloride and 2,4-diaminotoluene. The minor product was N-(5-benzamido-2-methylphenyl)benzamide which gave the following data: NMR (DMSOd$_6$) 2.2 (s, 3H), 7.21 (d, 1H), 7.5 (m, 7H), 7.84 (s, 1H), 7.98 (m, 4H), 9.81 (s, 1H), 10.23 (s, 1H); Mass M+H 331. The major product was N-(3-amino-4-methylphenyl)benzamide which gave the following data: NMR (DMSOd$_6$) 2.01 (s, 3H), 4.80 (s, 2H), 6.82 (m, 2H), 7.11 (s, 1H), 7.5 (m, 3H), 7.91 (m, 2H), (s, 1H); Mass M+H 227.

rr) The reactants were 3,4,5-trimethoxybenzoyl chloride and N-(3-amino-4-methylphenyl)-4-cyanobenzamide, 4-Dimethylaminopyridine (0.1 equivalents) was added to catalyse the reaction. On completion of the reaction, the reaction mixture was evaporated and the residue was triturated under 2N aqueous hydrochloric acid. The resultant solid was isolated, washed with a saturated aqueous sodium bicarbonate solution and with water and dried under vacuum at 55° C. The product gave the following data: NMR (DMSOd$_6$) 2.2 (s, 3H), 3.72 (s, 3H), 3.85 (s, 6H), 7.25 (d 1H), 7.33 (s, 2H), 7.56 (d, 1H), 7.81 (s, 1H), 8.0 (d, 2H), 8.1 (d, 2H), 9.87 (s, 1H), 10.46 (s, 1H); Mass M−H 444.

ss) 4-Dimethylaminopyridine (0.1 equivalents) was added to catalyse the reaction and the work-up described in Note rr) was used. The product gave the following data: NMR (DMSOd$_6$) 2.19 (s, 3H), 3.73 (s, 3H), 3.85 (s, 6H), 7.24 (d, 1H), 7.32 (s, 2H), 7.55 (m, 4H), 7.82 (s, 1H), 7.94 (d, 2H), 9.86 (br s, 1H), 10.22 (br s, 1H); Mass M−H 419.

tt) 4-Dimethylaminopyridine (0.1 equivalents) was added to catalyse the reaction and the work-up described in Note rr) was used. The product gave the following data: NMR (DMSOd$_6$) 2.2 (s, 3H), 3.73 (s, 3H), 3.84 (s, 6H), 7.25 (d, 1H), 7.32 (s, 2H), 7.58 (d, 1H), 7.78 (m, 2H), 7.95 (d, 1H), 8.25 (m, 2H), 9.86 (s, 1H), 10.44 (s, 1H); Mass M−H 487.

uu) The reactants were 3-morpholinobenzoyl chloride and N-(5-amino-2-methylphenyl)-3,4,5-trimethoxybenzamide. On completion of the reaction, the reaction mixture was evaporated and the residue was azeotroped with toluene. The resultant residue was stirred under methanol for 30 minutes. The solid so obtained was isolated and dried. The product gave the following data: NMR (DMSOd$_6$) 2.2 (s, 3H), 3.2 (t, 4H), 3.74 (m, 7H), 3.84 (s, 6H), 7.13 (m, 1H), 7.22 (d, 1H), 7.32 (s, 2H), 7.36 (d, 1H), 7.43 (s, 1H), 7.58 (d, 1H), 7.79 (s, 1H), 9.84 (s, 1H), 10.12 (s, 1H); Mass M+H 506.

The 3-morpholinobenzoyl chloride used as a starting material was prepared as follows:

A mixture of ethyl 3-bromobenzoate (1.92 ml), morpholine (1.25 ml), 2,2'-bis(diphenylphosphino)-1,1'-binaphthyl (0.336 g), sodium tert-butoxide (1.615 g) and tris(dibenzylideneacetone)dipalladium(0) (0.33 g) and toluene (25 ml) was stirred and heated to 90° C. for 18 hours under argon. The reaction mixture was allowed to cool to ambient temperature and extracted with 1N aqueous hydrochloric acid. The aqueous phase was basified with concentrated sodium hydroxide solution and extracted with ethyl acetate. The organic phase was dried (MgSO$_4$) and evaporated. The residual oil was purified by column chromatography on silica gel using a 47:3 mixture of methylene chloride and methanol as eluent. There was thus obtained N-(3-morpholinobenzoyl)morpholine (0.45 g).

A mixture of the material so obtained. 5M sodium hydroxide solution (2.5 ml) and butanol (2 ml) was stirred and heated to 115° C. for 18 hours. The mixture was evaporated and the residue was acidified by the addition of 1N aqueous hydrochloric acid solution (12.5 ml). The resultant precipitate was isolated, washed with water and dried to give 3-morpholinobenzoic acid (0.15 g); NMR (DMSOd$_6$) 3.1 (t, 4H), 3.73 (t, 4H), 7.19 (d, 1H), 7.32 (d, 1H), 7.38 (t, 1H), 7.42 (s, 1H).

Oxalyl chloride (0.14 ml) was added to a solution of 3-morpholinobenzoic acid (0.28 g) in methylene chloride (10 ml) which contained DMF (2 drops). The reaction mixture was stirred for 18 hours at ambient temperature. The mixture was evaporated and azeotroped with toluene to give 3-morpholinobenzoyl chloride (0.3 g); Mass M+H 222.

vv) The product gave the following data: m.p. 235–236° C.: NMR (DMSOd$_6$) 2.19 (s, 3H), 2.95 (s, 6H), 6.9 (m, 1H), 7.2 (m, 3H), 7.3 (t, 1H), 7.48 (t, 1H), 7.56 (m, 1H), 7.78 (m, 2H), 7.97 (d, 1H), 8.14 (d, 1H), 10.02 (br s, 1H), 10.09 (br s, 1H); Mass M+H 453.

ww) The product gave the following data: m.p. 219–220° C.: NMR (DMSOd$_6$) 2.2 (s, 3H), 2.95 (s, 6H), 6.92 (d, 1H), 7.23 (m, 3H), 7.28 (t, 1H), 7.575 (m, 1H), 7.83 (m, 2H), 8.43 (m, 2H), 8.8 (d, 1H), 10.12 (br s, 1H), 10.33 (br s, 1H); Mass M−H 417.

xx) On completion of the reaction, the reaction mixture was washed with water and with a saturated aqueous sodium bicarbonate solution. The mixture was evaporated and the residue was azeotroped with toluene. The resultant residue was purified by column chromatography using a 9:1 mixture of methylene chloride and methanol as eluent. The product gave the following data: NMR (DMSOd$_6$) 2.2 (s, 3H), 3.19 (s, 8H), 3.78 (s, 8H), 7.18 (d, 2H), 7.21 (d, 1H), 7.39 (m, 4H), 7.43 (s, 1H), 7.50 (s, 1H), 7.58 (m, 1H), 7.8 (s, 1H), 9.82 (s, 10.12 (s, 1H); Mass M+H 501.

yy) The reactants were benzoyl chloride and N-(5-amino-2-methylphenyl)-3-(4-methylpiperazin-1-ylmethyl) benzamide. On completion of the reaction, the reaction mixture was washed with water and with a saturated aqueous sodium bicarbonate solution. The mixture was evaporated and the residue was triturated under a mixture of diethyl ether and ethyl acetate. The product so obtained gave the following data: Mass M+H 443.

The N-(5-amino-2-methylphenyl)-3-(4-methylpiperazin-1-ylmethyl)benzamide used as starting material was prepared as follows:

3-Chloromethylbenzoyl chloride (24.8 ml) was added to a stirred mixture of 2-methyl-5-nitroaniline (26.6 g), triethylamine (49 ml) and methylene chloride (800 ml) and the mixture was stirred at ambient temperature for 16 hours. The precipitate was isolated, washed with 1N aqueous hydrochloric acid solution and with diethyl ether and dried under vacuum at 40° C. There was thus obtained 3-chloromethyl-N-(2-methyl-5-nitrophenyl)benzamide (43.5 g); NMR (DMSOd$_6$) 2.38 (s, 3H), 2.85 (s, 2H), 7.53–7.58 (m, 2H), 7.67 (d, 1H), 7.95(d, 1H), 8.01–8.04 (m, 2H), 8.32 (s, 1H), 10.19 (s, 1H); Mass M+H$^+$ 305.

1-Methylpiperazine (8.03 ml) was added to a stirred mixture of a portion (20 g) of the material so obtained, potassium carbonate (18.2 g) and acetone (750 ml) and the mixture was heated to 54° C. and stirred for 16 hours. The resultant solution was evaporated and the residue was dissolved in methylene chloride. The organic solution was washed with water and evaporated. There was thus obtained N-(2-methyl-5-nitrophenyl)-3-(4-methylpiperazin-1-ylmethyl)benzamide (26.4 g); NMR (DMSOd$_6$) 2.06 (s, 3H), 2.12 (s, 3H), 2.31–2.37 (m, 8H), 3.52 (s, 2H), 7.48–7.57 (m, 3H), 7.87 (d, 2H), 8.01 (m, 1H), 8.33 (s, 1H); Mass M+H 369.

Iron powder was added to a stirred mixture of a portion (18.0 g) of the material so obtained, ethanol (500 ml), water (50 ml) and acetic acid (10 ml). The resultant mixture was stirred and heated to reflux for 5 hours. Water (50 ml) was added and the mixture was basified by the addition of sodium carbonate. The mixture was filtered and the filtrate was evaporated to dryness. The residue was triturated under water and the resultant solid was isolated and dried under vacuum at 40° C. There was thus obtained N-(5-amino-2-methylphenyl)-3-(4-methylpiperazin-1-ylmethyl)benzamide (11.1 g); NMR (DMSOd$_6$) 2.03 (s, 3H), 2.13 (s, 3H), 2.24–2.4 (m, 8H), 3.5 (s, 2H), 4.86 (s, 2H) 6.35 (d, 1H), 6.57 (s, 1H), 6.86 (d, 1H), 7.40–7.48 (m, 2H), 7.78–7.83 (m, 2H), 9.57 (s, 1H); Mass M+H$^+$ 339.

zz) The variation of the work-up described in Note yy) was used. The product so obtained gave the following data: Mass M+H 511.

aaa) The variation of the work-up described in Note yy) was used. The product so obtained gave the following data: Mass M+H 461.

bbb) The variation of the work-up described in Note yy) was used. The product so obtained gave the following data: Mass M+H 461.

ccc) The variation of the work-up described in Note yy) was used. The product so obtained gave the following data: Mass M+H 477.

ddd) The variation of the work-up described in Note yy) was used. The product so obtained gave the following data: Mass M+H 477.

eee) The following variation of the procedure of Example 6 was used. A mixture of 4-chlorobenzoyl chloride (0.4 mmol), N-(5-amino-2-methylphenyl)-3-(4-methylpiperazin-1-ylmethyl)benzamide (0.44 mmol) and pyridine (5 ml) was stirred and heated to 70° C. for 16 hours. The resultant mixture was evaporated and the residue was partitioned between methylene chloride and a saturated aqueous sodium bicarbonate solution. The organic phase was evaporated and the residue was triturated under ethyl acetate. The product so obtained gave the following data: NMR (DMSOd$_6$) 2.13 (s, 3H), 2.19 (s, 3H), 2.25–2.37 (m, 8H), 3.51 (s, 2H), 7.22 (d, 1H), 7.45–7.51 (m, 2H), 7.54–7.59 (m, 3H), 7.81–7.87 (m, 3H), 7.97 (d, 2H), 9.88 (s, 1H), 10.28 (s, 1H); Mass M+H 477.

fff) An analogous procedure to that described in Note eee) was used. The product so obtained gave the following data: NMR (DMSOd$_6$) 2.13 (s, 3H), 2.19 (s, 3H), 2.25–2.37 (m, 8H), 3.51 (s, 2H), 7.22 (d, 1H), 7.38–7.58 (m, 6H), 7.75 (s, 1H), 7.85 (d, 2H), 9.88 (s, 1H), 10.44 (s, 1H); Mass M+H 479.

ggg) The variation of the work-up described in Note yy) was used. The product so obtained gave the following data: Mass M+H 479.

hhh) The variation of the work-up described in Note yy) was used. The product so obtained gave the following data: Mass M+H 511.

iii) The variation of the work-up described in Note yy) was used. The product so obtained gave the following data: Mass M+H 511.

jjj) An analogous procedure to that described in Note eee) was used. The product so obtained gave the following data: NMR (DMSOd$_6$) 2.14 (s, 3H), 2.17 (s, 3H), 2.25–2.4 (m, 8H), 3.51 (s, 2H), 3.88 (s, 3H), 7.05 (t, 1H), 7.14–7.22 (m, 2H), 7.45–7.5 (m, 4H), 7.62 (d, 1H), 7.78 (s, 1H), 7.85 (d, 2H), 9.9 (s, 1H), 10.06 (s, 1H); Mass M+H 473.

kkk) The variation of the work-up described in Note yy) was used. The product so obtained gave the following data: Mass M+H 473.

lll) The variation of the work-up described in Note yy) was used. The product so obtained gave the following data: Mass M+H 487.

mmm) The variation of the work-up described in Note yy) was used. The product so obtained gave the following data: Mass M+H 503.

nnn) The variation of the work-up described in Note yy) was used. The product so obtained gave the following data: Mass M+H 468.

ooo) The variation of the work-up described in Note yy) was used. The product so obtained gave the following data: Mass M+H 501.

ppp) The reactants were 3-morpholinobenzoyl chloride and N-(5-amino-2-methylphenyl)-3-(4-methylpiperazin-1-ylmethyl)benzamide. On completion of the reaction, the reaction mixture was washed with water and with a saturated aqueous sodium bicarbonate solution. The mixture was evaporated and the residue was purified by column chromatography on an ion exchange column (isolute SCX column from International Sorbent Technology Limited, Hengoed, Mid-Glamorgan, UK) using a 99:1 mixture of methanol and a saturated aqueous ammonium hydroxide solution as eluent. The product so obtained gave the following data: NMR (DMSOd$_6$) 2.13

(s, 3H), 2.19 (s, 3H), 2.31–2.38 (m, 8H), 3.15–3.18 (m, 4H), 3.52 (s, 2H), 3.73–3.76 (m, 4H), 7.1–7.14 (m, 1H), 7.2 (d, 1H), 7.22–7.38 (m, 2H), 7.4–7.52 (m, 3H), 7.52–7.6 (m, 1H), 7.4–7.87 (m, 2H), 9.84 (s, 1H) 10.11 (s, 1H); Mass M+H 528.

EXAMPLE 10

N-[5-(4-Hydroxybenzamido)-2-methylphenyl]-3,4-dimethoxybenzamide

10% Palladium-on-carbon (0.5 g) was added to a stirred suspension of N-[5-(4-benzyloxybenzamido)-2-methylphenyl]-3,4-dimethoxybenzamide (3.97 g) in methanol (500 ml) and the mixture was stirred under an atmosphere of hydrogen. After cessation of hydrogen uptake, the mixture was filtered and the filtrate was evaporated. The solid so obtained was washed with diethyl ether and dried under vacuum at 60° C. There was thus obtained the title compound (2.93 g), m.p. 258–259° C.;

NMR Spectrum: (DMSOd$_6$) 2.17 (s, 3H), 3.83 (s, 6H), 6.84 (d, 2H), 7.05 (d, 1H), 7.19 (d, 1H), 7.54 (m, 2H), 7.65 (d, 1H), 7.78 (d, 1H), 7.84 (d, 2H), 9.74 (br s, 1H); Mass Spectrum: M–H$^-$ 405. Elemental Analysis: Found C, 66.9; H, 5.3; N, 6.7; $C_{23}H_{22}N_2O_5$.0.2H$_2$O requires C, 67.4; H, 5.5; N, 6.8%.

EXAMPLE 11

N-[5-(3-Hydroxybenzamido)-2-methylphenyl]-3,4-dimethoxybenzamide

Using an analogous procedure to that described in Example 10, N-[5-(3-benzyloxybenzamido)-2-methylphenyl]-3,4-dimethoxybenzamide was hydrogenolysed to give the title compound in 72% yield; m.p. 182–183° C.;

NMR Spectrum: (DMSOd$_6$) 2.17 (s, 3H), 3.83 (s, 6H), 6.95 (m, 1H), 7.06 (d, 1H), 7.22 (d, 1H), 7.32 (m, 2H), 7.36 (d, 1H), 7.55 (m, 2H), 7.63 (m, 1H), 7.82 (d, 1H), 9.68 (br s, 2H), 9.75 (br s, 1H), 10.13 (br s, 1H); Mass Spectrum: M–H$^-$ 405.

EXAMPLE 12

N-[5-(3-Dimethylaminobenzamido)-2-methylphenyl]-4-acetylbenzamide

4-Acetylbenzoic acid (0.164 g) was added to a stirred mixture of N-(3-amino-4-methylphenyl)-3-dimethylaminobenzamide (0.135 g), diisopropylethylamine (0.325 ml), 2-(7-azabenzotriazol-1-yl)-1,1,3,3-tetramethyluronium hexafluorophosphate(V). (0.39 g) and DMF (10 ml) and the mixture was stirred at ambient temperature for 16 hours. The resultant solution was evaporated. The residue was dissolved in methylene chloride and the solution was washed in turn with water, a saturated aqueous solution of sodium bicarbonate and brine, dried (MgSO$_4$) and evaporated. The residue was triturated under a mixture of ethyl acetate and isohexane. The resultant solid was isolated, washed with ethyl acetate and dried under vacuum at 40° C. There was thus obtained the title compound as a solid (0.091 g); NMR Spectrum: (DMSO$_6$) 2.19 (s, 3H), 2.63 (s, 3H), 2.95 (s, 6H), 6.91 (d, 1H), 7.29 (m, 4H), 7.62 (d, 1H), 7.82 (s, 1H), 8.1 (m, 4H), 10.12 (s, 1H), 10.13 (s, 1H); Mass Spectrum: M+H$^+$ 416.

EXAMPLE 13

N-[5-(3-Aminobenzamido)-2-methylphenyl]-3,4-dimethoxybenzamide

10% Palladium-on-carbon (0.13 g) was added to a stirred solution of N-[5-(3-nitrobenzamido)-2-methylphenyl]-3,4-dimethoxybenzamide (1.27 g) in methanol (150 ml) and the mixture was stirred under an atmosphere pressure of hydrogen. After cessation of hydrogen uptake, the catalyst was removed by filtration and the filtrate was evaporated. The residue was washed with diethyl ether and dried under vacuum at 60° C. There was thus obtained the title compound (1.02 g), m.p. 179–180° C.;

NMR Spectrum: (DMSOd$_6$) 2.15 (s, 3H), 3.82 (s, 6H), 5.25 (s, 2H), 6.72 (d, 1H), 7.05 (br m, 3H), 7.1 (t, 1H), 7.19 (d, 1H), 7.52 (m, 1H), 7.55 (d, 1H), 7.63 (m, 1H), 7.79 (d, 1H), 9.76 (br s, 1H), 10.02 (br s, 1H); Mass spectrum: M+H$^+$ 406; Elemental Analysis: Found C, 66.3; H, 5.3; N, 9.9; $C_{23}H_{23}N_3O_4$.0.5H2O requires C, 66.7; H, 5.8. N, 10.1%.

EXAMPLE 14

N-[5-(3-Dimethylaminobenzamido)-2-methylphenyl]-4-carboxybenzamide

A 2N sodium hydroxide solution (0.27 ml) was added to a stirred suspension of N-[5-(3-dimethylaminobenzamido)-2-methylphenyl]-4-methoxycarbonylbenzamide (0.077 g) in a mixture of methanol (10 ml) and water (2 ml). The reaction mixture was stirred at ambient temperature for 16 hours. The mixture was evaporated and the residue was dissolved in water. The aqueous solution was and extracted with ethyl acetate, acidified to pH 5 by the addition of dilute hydrochloric acid and extracted with ethyl acetate. The resultant organic extract was evaporated and the residue was dried at 40° C. There was thus obtained the title compound (0.006 g); Mass Spectrum: M–H$^-$ 416.

EXAMPLE 15

N-[5-(4-Morpholinomethylbenzamido)-2-methylphenyl]-3,4-dimethoxybenzamide

Morpholine (0.03 ml) was added to a stirred suspension of N-[5-(4-chloromethylbenzamido)-2-methylphenyl]-3,4-dimethoxybenzamide (0.15 g) and potassium carbonate (0.094 g) in acetone (10 ml). The mixture was heated to 54° C. and stirred for 16 hours. The resultant solution was evaporated and the residue was dissolved in methylene chloride. The organic solution was washed with water and evaporated. The residue was triturated under a mixture of ethyl acetate and diethyl ether. The resultant white solid was isolated and dried under vacuum at 40° C. There was thus obtained the title compound (0.135 g); NMR Spectrum: (DMSOd$_6$) 2.18 (s, 3H), 2.35 (t, 2H), 3.28 (s, 2H), 3.55 (t, 4H), 3.82 (s, 6H), 7.07 (d, 1H), 7.21 (d, 1H), 7.43 (d., 2H), 7.55 (m, 2H), 7.61 (d, 1H), 7.81 (s, 1H), 7.89 (d, 2H), 9.78 (s, 1H), 10.16 (s, 1H); Mass Spectrum: M+H$^+$ 490.

The N-[5-(4-chloromethylbenzamido)-2-methylphenyl]-3,4-dimethoxybenzamide used as a starting material was prepared as follows 4-Chloromethylbenzoyl chloride (0.73 g) was added dropwise to a stirred mixture of N-(5-amino-2-methylphenyl)-3,4-dimethoxybenzamide (1 g), triethylamine (0.98 ml) and methylene chloride (80 ml) and the mixture was stirred at ambient temperature for 16 hours. A 1N hydrochloric acid solution (10 ml) was added and the resultant solution was stirred at ambient temperature for 1 hour. The resultant white solid was filtered off, washed with water and with diethyl ether, dried under vacuum at 40° C. to give the required starting material (1.35 g); NMR Spectrum: (DMSOd$_6$) 2.18 (s, 3H), 3.82 (s, 6H), 4.82 (s, 2H), 7.06 (d, 1H), 7.21 (d, 1H), 7.58 (m, 5H), 7.81 (s, 1H), 7.94 (d, 2H), 9.76 (s, 1H), 10.23 (s, 1H); Mass Spectrum: M+H$^+$ 439.

EXAMPLE 16

N-{5-[3-(4-Methylpiperazin-1-ylmethyl)benzamido]-2-methylphenyl}-3,4dimethoxybenzamide Using an analogous procedure to that described in Example 15, 1-methylpiperazine was reacted with N-[5-(3-chloromethylbenzamido)-2-methylphenyl]-3,4-dimethoxybenzamide to give the title compound in 17% yield; NMR Spectrum: (DMSOd$_6$) 2.14 (s, 3H), 2.18 (s, 3H), 2.36 (m, 8H), 3.51 (s, 2H), 3.82 (s, 6H), 7.07 (d, 1H), 7.47 (m, 2H), 7.61 (m, 3H), 7.82 (m, 3H), 9.75 (s, 1H), 10.18 (s, 1H); Mass Spectrum: M+H$^+$ 503.

The N-[5-(3-chloromethylbenzamido)-2-methylphenyl]-3,4-dimethoxybenzamide used as a starting material was prepared as follows 3-Chloromethylbenzoyl chloride (0.6 g) was added to a stirred mixture of N-(5-amino-2-methylphenyl)-3,4-dimethoxybenzamide (1 g), triethylamine (0.98 ml) and methylene chloride (100 ml) and the resultant mixture was stirred at ambient temperature for 16 hours. The mixture was washed with 1N hydrochloric acid and with a saturated aqueous solution of sodium bicarbonate, dried (MgSO$_4$) and evaporated. The residue was triturated under a mixture of ethyl acetate and diethyl ether. The resultant white solid was isolated and dried under vacuum at 40° C. to give the required starting material (1.35 g); NMR Spectrum: 2.19 (s, 3H), 3.82 (s, 6H), 4.84 (s, 2H), 7.06 (d, 1H), 7.23 (d, 1H), 7.57 (m, 5H), 7.8 (s, 1H), 7.9 (d, 1H), 8.0 (s, 1H), 9.76 (s, 1H), 10.26 (s, 1H); Mass Spectrum: M+H$^+$ 439.

EXAMPLE 17

N-[5-(3-Cyclohexylpropionamido)-2-methylphenyl]-4-methoxybenzamide

4-Methoxybenzoyl chloride (0.064 ml) was added to a stirred mixture of N-(3-amino-4-methylphenyl)-3-cyclohexylpropionamide (J. Med. Chem., 1996, 39, 3343–3356; 0.13 g), triethylamine (0.14 ml) and methylene chloride (5 ml) and the mixture was stirred at ambient temperature for 16 hours. The resultant mixture was washed in turn with a 5% aqueous citric acid solution, with a saturated aqueous solution of sodium bicarbonate and with brine, dried (MgSO$_4$) and evaporated. The residue was triturated under a mixture of ethyl acetate and isohexane. The resultant solid was isolated and dried under vacuum at 40° C. There was thus obtained the title compound (0.159 g); NMR Spectrum: (DMSOd$_6$) 0.89 (m, 2H), 1.19 (m, 4H), 1.47 (m, 2H), 1.66 (m, 5H), 2.13 (s, 3H), 2.3 (t, 2H), 3.82 (s, 3H), 7.03 (d, 2H), 7.12 (d, 1H), 7.37 (d, 1H), 7.61 (s, 1H), 7.93 (d, 2H), 9.67 (s, 1H), 9.8 (s, 1H); Mass Spectrum: M+H$^+$ 395.

EXAMPLE 18

N-[5-(3-Cyclohexylpropionamido)-2-methylphenyl]-4-acetylbenzamide

A solution of oxalyl chloride (0.1 ml) in methylene chloride (0.5 ml) was added to a stirred mixture of 4-acetylbenzoic acid (0.098 g). DMF (3 drops) and methylene chloride (2 ml). The reaction mixture was stirred and heated to 40° C. for 3 hours. The mixture was evaporated to dryness. The residue was dissolved in methylene chloride (2 ml). DMF (3 drops) was added, followed by the addition of a mixture of N-(3-amino-4-methylphenyl)-3-cyclohexylpropionamide (0.138 g) and pyridine (0.2 ml) in methylene chloride (4 ml). The resultant mixture was stirred at ambient temperature for 18 hours. The reaction mixture was evaporated and the residue was triturated under ethyl acetate. The resultant solid was washed with water and dried to give the title product (0.153 g); NMR Spectrum: (DMSOd$_6$) 0.8 (m, 2H), 1.1 (m, 4H), 1.39 (m, 2H), 1.60 (m, 5H) 2.08 (s, 3H), 2.2 (t, 2H), 2.53 (s, 3H), 7.06 (d, 1H), 7.28 (m, 1H), 7.56 (d, 1H), 7.86 (m, 1H), 7.97 (s, 4H), 8.37 (m, 1H), 8.77 (m, 1H), 9.74 (s, 1H), 9.92 (s, 1H); Mass Spectrum: M+H$^+$ 407.

EXAMPLE 19

Using an analogous procedure to that described in Example 17 or Example 18, the appropriate benzoyl chloride was reacted with the appropriate aniline to give the compounds described in Table II.

TABLE II

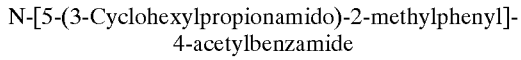

| No. | (R$^1$)$_m$ | Method | Note |
|---|---|---|---|
| 1 | 4-ethoxy | Ex. 17 | a |
| 2 | 4-butoxy | Ex. 18 | b |
| 3 | 3,4-dimethoxy | Ex. 17 | c |
| 4 | 3,5-dimethoxy | Ex. 18 | d |
| 5 | 3,4-diethoxy | Ex. 17 | e |
| 6 | 3,4,5-trimethoxy | Ex. 17 | f |
| 7 | 3-methoxycarbonyl | Ex. 18 | g |
| 8 | 3-cyano | Ex. 18 | h |
| 9 | 4-cyano | Ex. 17 | i |
| 10 | 3-methoxy-4-hydroxy | Ex. 18 | j |
| 11 | 2-nitro-4-methoxy | Ex. 18 | k |

Notes
a) The product gave the following data: NMR (DMSOd$_6$) 0.9 (m, 2H), 1.2 (m, 4H), 1.37 (t, 3H), 1.5 (m, 2H), 1.7 (m, 5H) 2.17 (s, 3H), 2.28 (t, 2H), 4.12 (m, 2H), 7.03 (d, 2H), 7.14 (d, 1H), 7.38 (m, 1H), 7.64 (d, 1H), 7.95 (d, 2H), 9.65 (s, 1H), 9.8 (s, 1H); Mass M+H 409.
b) 4-Dimethylaminopyridine (0.15 equivalents) was added to catalyse the reaction. The product gave the following data: NMR (DMSOd$_6$) 0.89 (m, 5H), 1.12 (m, 4H), 1.53 (m, 11H), 2,32 (s, 3H), 2.28 (t, 2H), 4.02 (t, 2H), 7.0 (d, 2H), 7.12 (d, 1H), 7.38 (d, 1H), 7.60 (s, 1H), 7.9 (d, 2H), 9.64 (s, 1H), 9.78 (s, 1H); Mass M+H 437.
c) The product gave the following data: NMR (DMSOd$_6$) 0.89 (m, 2H), 1.19 (m, 4H), 1.45 (m, 7H), 2.14 (s, 3H), 2.27 (t, 2H), 3.82 (s, 6H), 7.04 (d, 1H), 7.14 (d, 1H), 7.36 (s, 1H), 7.52 (s, 1H), 7.60 (s, 1H), 7.62 (s, 1H), 9.68 (s, 1H), 9.8 (s, 1H); Mass M+H 425.
d) The product gave the following data: NMR (DMSOd$_6$) 0.8 (m, 2H), 1.1 (m, 4H), 1.42 (m, 2H), 1.6 (m, 5H) 2.08 (s, 3H), 2.23 (t, 2H), 3.75 (s, 6H), 6.62 (t, 1H), 7.08 (m, 3H), 7.3 (m, 1H), 7.56 (d, 1H), 7.88 (t, 1H), 8.38 (m, 1H), 8.79 (m, 1H), 9.73 (s, 1H), 9.76 (s, 1H); Mass M+H 425.
e) The benzoyl chloride was prepared by the dropwise addition of oxalyl chloride (0.75 mmol) to a stirred mixture of 3,4-diethoxybenzoic acid (0.75 mmol) and DMF (a few drops) which had been cooled to 0° C. The mixture was allowed to warm to ambient temperature and was stirred for four hours. The resultant solution was evaporated and the resultant acid chloride was used without further purification. The benzamide product gave the following data: Mass M+H 453.
f) The product gave the following data: NMR (DMSOd$_6$) 0.87 (m, 2H), 1.12 (m, 4H), 1.45 (m, 2H), 1.64 (m, 5H), 2.13 (s, 3H), 2.27 (t, 2H), 3.71 (s, 3H), 3.83 (s, 6H), 7.14 (d, 2H), 7.29 (s, 1H), 7.33 (d, 1H), 7.61 (s, 1H), 9.81 (s, 2H); Mass M+H 455.

g) The product gave the following data: NMR (DMSOd₆) 0.9 (m, 2H), 1.15 (m, 4H), 1.49 (m, 2H), 1.65 (m, 5H) 2.18 (s, 3H), 2.28 (t, 2H), 3.92 (s, 3H), 7.17 (d, 1H), 7.38 (m, 1H), 7.68 (m, 2H), (d, 1H) 8.57 (s, 1H), 9.84 (s, 1H), 10.1 (s, 1H); Mass M+H 423.

h) The product gave the following data: Mass M+H 390.

i) The product gave the following data: Mass M+H 390.

j) The product gave the following data: NMR (DMSOd₆) 0.9 (m, 2H), 1.25 (m, 4H), 1.5 (m, 2H), 1.7 (m, 5H) 2.2 (s, 3H), 2.62 (t, 2H), 3.87 (s, 3H), 6.86 (d, 1H), 7.15 (d, 1H), 7.35 (m, 1H), 7.5 (m, 1H), 7.6 (d, 1H), 7.64 (d, 1H), 9.55 (s, 1H), 9.57 (s, 1H), 9.75 (s, 1H); Mass M+H 411.

k) The product gave the following data: Mass M+H 439.

EXAMPLE 20

N-[5-(3-Cyclohexylpropionamido)-2-methylphenyl]-4-carboxybenzamide

A 2N sodium hydroxide solution (0.27 ml) was added to a stirred suspension of N-[5-(3-cyclohexylpropionamido)-2-methylphenyl]-4-methoxycarbonylbenzamide (0.087 g) in a mixture of methanol (10 ml) and water (2 ml). The reaction mixture was stirred at ambient temperature for 16 hours. The mixture was evaporated and the residue was dissolved in water. The aqueous solution was and extracted with ethyl acetate, acidified to pH 5 by the addition of dilute hydrochloric acid and extracted with ethyl acetate. The resultant organic extract was evaporated and the residue was dried at 40° C. There was thus obtained the title compound (0.016 g); NMR Spectrum: (DMSOd₆) 0.91 (m, 2H), 1.16 (m, 4H), 1.47 (m, 2H), 1.66 (m, 5H), 2.15 (s, 3H), 2.28 (t, 2H), 7.15 (d, 1H), 7.36 (d, 1H), 7.64 (s, 1H), 8.06 (d, 4H), 9.82 (s, 1H), 10.04 (s, 1H); Mass Spectrum: M–H⁻ 407.

The N-[5-(3-cyclohexylpropionamido)-2-methylphenyl]-4-methoxycarbonylbenzamide used as a starting material was obtained as follows:

4-Methoxycarbonylbenzoyl chloride (0.198 g) was added to a stirred mixture of N-(3-amino-4-methylphenyl)-3-cyclohexylpropionamide (0.13 g), 4-dimethylaminopyridine (0.06 g), triethylamine (0.139 ml) and methylene chloride (10 ml) and the mixture was stirred at ambient temperature for 16 hours. The resultant precipitate was filtered off and washed in turn with methylene chloride, ethyl acetate and 1N hydrochloric acid. The solid was dried under vacuum at 40° C. to give the title product (0.105 g); NMR Spectrum: (DMSOd₆) 0.78 (m, 2H), 1.14 (m, 4H), 1.25 (m, 2H), 1.53 (m, 5H), 2.15 (s, 3H), 2.28 (t, 2H), 3.88 (s, 3H), 7.15 (d, 1H), 7.37 (d 2H), 7.64 (s, 1H), 8.07 (s, 4H), 9.82 (s, 1H), 10.05 (s, 1H); Mass Spectrum: M+H⁺ 432.

EXAMPLE 21

N-[5-(3-Cyclobexylpropionamido)-2-methylphenyl]-3-carboxybenzamide

Using an analogous procedure to that described in Example 20, N-[5-(3-cyclohexylpropionamido)-2-methylphenyl]-3-methoxycarbonylbenzamide was hydrolysed to give the title compound in 16% yield; Mass Spectrum: M–H⁻ 407.

EXAMPLE 22

N-[5-(5-Cyclobexylpentanoamido)-2-methylphenyl]-4-hydroxybenzamide

A solution of 1-(3-dimethylaminopropyl)-3-ethylcarbodiimide hydrochloride (0.096 g) in methylene chloride (3 ml) was added to a stirred mixture of N-(5-amino-2-methylphenyl)-4-hydroxybenzamide (0.13 g), 5-cyclohexylpentanoic acid (0.092 g) and DMF (0.5 ml) and the reaction mixture was stirred at ambient temperature for 5 hours. The mixture was evaporated and the residue was partitioned between ethyl acetate and 1N hydrochloric acid solution. The organic phase was evaporated to give the title compound (0.083 g);

NMR Spectrum: (DMSOd₆) 0.85 (m, 2H), 1.2 (m, 8H), 1.65 (m, 7H) 2.15 (s, 3H), 2.28 (t, 2H), 6.86 (d, 2H), 7.14 (d, 1H), 7.3 (m, 1H), 7.62 (d, 1H), 7.86 (d, 2H), 9.54 (s, 1H), 9.77 (s, 1H), 10.01 (s, 1H); Mass Spectrum: M+H⁺ 409.

EXAMPLE 23

The following compounds are described in *J. Med. Chem.*, 1996, 39, 3343–3356 and were prepared using analogous procedures. The compounds possess p38 kinase inhibitory activity.

N-[5-(3-cyclopentylpropionamido)-2-methylphenyl]-4-hydroxybenzamide;

N-[5-(3-cyclohexylpropionamido)-2-methylphenyl]-3-hydroxybenzamide;

N-[5-(3-cyclohexylpropionamido)-2-methylphenyl]-4-hydroxybenzamide; and

N-[5-(3-cyclohexylpropionamido)-2-methylphenyl]-4-aminobenzamide.

EXAMPLE 24

N-[5-(4-Cyclohexylbutyrylamino)-2-methylphenyl]-4-hydroxybenzamide

4-Cyclohexylbutyric acid (255 mg) was added to a solution of N-(5-amino-2-methylphenyl)-4-hydroxybenzamide (242 mg) in DMF (3.0 ml). The mixture was stirred and a solution of 1-(3-dimethylamino)propyl-3-ethylcarbodiimide hydrochloride (287 mg) added. The mixture was stirred overnight at ambient temperature, evaporated to a small volume and ethyl acetate (5 ml) was added. The mixture was washed with aqueous sodium bicarbonate solution (5 ml), water (5 ml), 2M aqueous hydrochloric acid (5 ml), water (5 ml) and brine (5 ml). The organic phase was filtered through a megabond elute column, eluting with ethyl acetate (25 ml) and evaporated to dryness. The residue was triturated with ether, filtered, washed with ether and dried to give the title compound (280 mg), m.p. 159–160° C.;

NMR Spectrum: (DMSOd₆) 0.75–1.0 (m, 2H), 1.05–1.35 (m, 6H), 1.5–1.78 (m, 7H), 2.18 (s, 3H), 2.27 (t, 2H), 6.86 (d, 2H), 7.14 (d, 1H), 7.39 (m, 1H), 7.63 (d, 1H), 7.86 (d, 2H), 9.56 (s, 1H), 9.7 (s, 1H), 10.0 (s, 1H); Mass Spectrum: M+H⁺ 395, (M+Na)⁺ 417; Microanalysis: % Theory C 73.1, H 7.66, N 7.1%, % Found C 73.3, H 7.7, N 7.0%.

EXAMPLE 25

N-[2-Methyl-5-(3-trifluoromethylbenzamido)phenyl]-3,4-dimethoxybenzamide

Phosphoryl chloride (0.045 ml) was added to a stirred solution of N-(3-amino-4-methylphenyl)-3-trifluoromethylbenzamide (0.119 g) and 3,4-dimethoxybenzoic acid (0.088 g) in pyridine (1 ml) which had been cooled to 0° C. The mixture was allowed to warm to ambient temperature and was stirred for 16 hours. The resultant mixture was poured into a 2N aqueous hydrochloric acid solution. The resultant solid was isolated, washed with a saturated aqueous sodium bicarbonate solution and with isohexane and dried under vacuum at 55° C. There was thus obtained the title compound (0.107 g); NMR Spectrum: (DMSOd$_6$) 2.2 (s, 3H), 3.82 (s, 6H), 7.07 (d, 1H), 7.23 (d, 1H), 7.60 (m, 3H), 7.77 (m, 2H), 7.95 (d, 1H), 8.27 (m, 2H), 9.76 (s, 1H), 10.43 (s, 1H); Mass Spectrum: M–H$^-$ 457.

The N-(3-amino-4-methylphenyl)-3-trifluoromethylbenzamide used as starting material was prepared by the reaction of 3-trifluoromethylbenzoyl chloride with 4-methyl-3-nitroaniline and reduction of the resultant product using analogous procedures to those described in the portion of Example 8 which is concerned with the preparation of starting materials.

EXAMPLE 26

N-[5-(3-Morpholinomethylbenzamido)-2-methylphenyl]-3,4-dimethoxybenzamide

Using an analogous procedure to that described in Example 15, morpholine was reacted with N-[5-(3-chloromethylbenzamido)-2-methylphenyl]-3,4-dimethoxybenzamide to give the title compound in 84% yield; NMR Spectrum: (DMSOd$_6$) 2.18 (s, 3H), 2.37 (t, 4H), 3.52 (s, 2H), 3.56 (t, 4H), 3.82 (s, 6H), 7.07 (d, 1H), 7.21 (d, 1H), 7.43–7.59 (m, 2H), 7.52–7.64 (m, 3H), 7.79 (s, 1H), 7.89 (d, 2H), 9.78 (s, 1H), 10.16 (s, 1H); Mass Spectrum: M+H$^+$ 490.

EXAMPLE 27

N-[5-(4-Cyanobenzamido)-2-methylphenyl]-4-morpholinomethylbenzamide

A mixture of N-[5-(4-cyanobenzamido)-2-methylphenyl]-4-chloromethylbenzamide (0.1 g), morpholine (0.033 g), potassium carbonate (0.068 g) and acetone (5 ml) was stirred and heated to 55° C. for 16 hours. The reaction mixture was evaporated and the residue was triturated under water. The solid so obtained was isolated and dried under vacuum at 55° C. There was thus obtained the title compound (0.099 g); NMR Spectrum: (DMSOd$_6$) 2.2 (s, 3H), 2.38 (m, 4H), 3.52 (s, 2H), 3.58 (t, 4H), 7.23 (d, 1H), 7.45 (d, 2H), 7.57 (d, 1H), 7.82 (d, 1H), 7.93 (d, 2H), 8.0 (d, 2H), 8.1 (d, 2H), 9.85 (s, 1H), 10.45 (s, 1H); Mass Spectrum: M–H$^-$ 453.

The N-[5-(4-cyanobenzamido)-2-methylphenyl]-4-chloromethylbenzamide used as a starting material was obtained as follows:

Triethylamine (1.83 ml) was added to a stirred mixture of N-(3-amino-4-methylphenyl)-4-cyanobenzamide (3.0 g), 4-chloromethylbenzoyl chloride (2.48 g), 4-dimethylaminopyridine (0.146 g) and methylene chloride (50 ml) and the reaction mixture was stirred at ambient temperature for 16 hours. The mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. There was thus obtained the required compound (4.76 g); NMR Spectrum: (DMSOd$_6$) 2.2 (s, 3H), 4.84 (s, 2H), 7.25 (d, 1H), 7.57 (d, 3H), 7.83 (d, 1H), 7.98 (m, 4H), 8.1 (d, 2H), 9.93 (s, 1H), 10.46 (s, 1H); Mass Spectrum: M–H$^-$ 402.

EXAMPLE 28

Using an analogous procedure to that described in Example 27, the appropriate amine was reacted with the appropriate benzyl chloride to give the compounds described in Table III.

TABLE III

| No. | (R$^1$)$_m$ | R | Note |
|---|---|---|---|
| 1 | 3-piperazin-1-yl)methyl | hydrogen | a |
| 2 | 3-(4-propylpiperazin-1-yl)methyl | hydrogen | b |
| 3 | 3-(4-carbamoylpipendin-1-yl)methyl | hydrogen | c |
| 4 | 4-(4-methylhomopiperazin-1-yl)methyl | hydrogen | d |
| 5 | 3-(4-acetylpiperazin-1-yl)methyl | 3-trifluoromethyl | e |
| 6 | 4-(4-ethylpiperazin-1-yl)methyl | 3-trifluoromethyl | f |
| 7 | 4-(4-methylpiperazin-1-yl)methyl | 4-cyano | g |
| 8 | 3-(4-isopropylpiperazin-1-yl)methyl | 4-cyano | h |
| 9 | 3-(pyrrolidin-1-yl)methyl | 4-cyano | i |
| 10 | 3-morpholinomethyl | 4-cyano | j |
| 11 | 4-piperidinomethyl | 4-cyano | k |
| 12 | 4-(piperazin-1-yl)methyl | 4-cyano | l |
| 13 | 4-(4-methylpiperazin-1-yl)methyl | 4-cyano | m |

Notes a) The product gave the following data: NMR (DMSOd$_6$) 2.2 (s, 3H), 2.3 (m, 4H), 2.67 (m, 4H), 3.48 (s, 2H), 7.21 (d, 1H), 7.53 (m, 6H), 7.84 (m, 3H), 7.95 (d, 2H), 9.88 (s, 1H), 10.21 (s, 1H); Mass M–H 428.

The N-(5-benzamido-2-methylphenyl)-3-chloromethylbenzamide used as a starting material was prepared as follows:

Triethylamine (2.0 ml) was added to a stirred mixture of N-(3-amino-4-methylphenyl)benzamide (3.0 g), 3-chloromethylbenzoyl chloride (2.76 g), 4-dimethylaminopyridine (0.162 g) and methylene chloride (50 ml) and the reaction mixture was stirred at ambient temperature for 16 hours. The mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. There was thus obtained the required compound (5.1 g) which was used without further purification;

NMR (DMSOd$_6$) 2.19 (s, 3H), 4.85 (s, 2H), 7.23 (d, 1H), 7.55 (m, 5H), 7.66 (d, 1H), 7.84 (s, 1H), 7.95 (m, 3H), 8.05 (s, 1H), 9.96 (s, 1H), 10.22 (s, 1H); Mass M–H 377.

b) The product gave the following data: NMR (DMSOd$_6$) 0.91 (t, 3H), 1.40 (m, 2H), 2.19 (m, 5H), 2.37 (br s, 8H), 3.53 (s, 2H), 7.21 (d, 1H), 7.52 (m, 6H), 7.84 (m, 3H), 7.95 (d, 2H); Mass M–H 469.

c) The product gave the following data: NMR (DMSOd$_6$) 1.6 (m, 4H), 1.98 (m, 3H), 2.2 (s, 3H), 2.82 (br d, 2H), 3.51 (s, 2H), 6.65 (br s, 1H), 7.17 (br s, 1H), 7.21 (d, 1H), 7.52 (m, 6H), 7.83 (m, 3H), 7.95 (d, 2H); Mass M–H 469.

d) The product gave the following data: NMR (DMSOd$_6$) 1.7 (m, 2H), 2.2 (s, 3H), 2.24 (s, 3H), 2.58 (m 8H), 3.66 (s, 2H), 7.21 (d, 1H), 7.52 (m, 6H), 7.83 (m, 1H), 7.95 (m, 4H); Mass M–H 455.

The N-(5-benzamido-2-methylphenyl)-4-chloromethylbenzamide used as a starting material was prepared as follows:

Triethylamine (2.0 ml) was added to a stirred mixture of N-(3-amino-4-methylphenyl)benzamide (3.0 g), 4-chloromethylbenzoyl chloride (2.76 g) 4-dimethylaminopyridine (0.162 g) and methylene chloride (50 ml) and the reaction mixture was stirred at ambient temperature for 16 hours. The mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. There was thus obtained the required compound (4.96 g); NMR (DMSOd$_6$) 2.19 (s, 3H), 4.84 (s, 2H), 7.22 (d, 1H), 7.54 (m, 6H), 7.84 (s, 1H), 7.96 (m, 4H), 9.92 (s, 1H), 10.22 (s, 1H); Mass M–H 377.

e) The product gave the following data: NMR (DMSOd$_6$) 1.97 (s, 3H), 2.2 (s, 3H), 2.38 (m, 4H), 3.28 (br s, 2H), 3.42 (br s, 2H), 3.56 (s, 2H), 7.22 (d, 1H), 7.5 (m, 3H), 7.75 (t, 1H), 7.81 (s, 1H), 7.91 (m, 3H), 8.28 (m, 2H); Mass M–H 537.

The N-[5-(3-trifluoromethylbenzamido)-2-methylphenyl]-3-chloromethylbenzamide used as a starting material was prepared as follows:

A mixture of 3-trifluoromethylbenzoyl chloride (9.9 ml), 3-nitro-4-methylaniline (10 g) and pyridine (100 ml) was stirred and heated to 80° C. for 2 hours. The reaction mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. to give N-(4-methyl-3-nitrophenyl)-3-trifluoromethylbenzamide as a solid (21.9 g); NMR (DMSOd$_6$) 7.49 (d, 1H), 7.78 (m, 1H), 7.99 (m, 2H), 8.27 (m, 2H), 8.51 (s, 1H), 10.77 (s, 1H); Mass M–H 323.

Palladium on charcoal (1.0 g) was added to a solution of a portion (10 g) of the material so obtained in methanol (250 ml). Ammonium formate (19.0 g) was added and the resultant mixture was stirred and heated to reflux for 1 hour. The mixture was filtered through diatomaceous earth (Celite®) and the filtrate was evaporated. The residue was triturated under water. The resultant solid was isolated and dried under vacuum at 55° C. to give N-(3-amino-4-methylphenyl)-3-trifluoromethylbenzamide as a solid (7.98 g); NMR (DMSOd$_6$) 2.01 (s, 3H), 4.83 (s, 2H), 6.85 (m, 2H), 7.08 (s, 1H), 7.74 (t, 1H), 7.92 (d, 1H), 8.2 (d, 1H), 10.11 (s, 1H); Mass M–H 293.

Triethylamine (1.6 ml) was added to a stirred mixture of a portion (3.0 g) of the material so obtained, 3-chloromethylbenzoyl chloride (2.17 ml), 4-dimethylaminopyridine (0.125 g) and methylene chloride (50 ml) and the reaction was stirred at ambient temperature for 16 hours. The mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. There was thus obtained the required compound as a solid (5.17 g); NMR (DMSOd$_6$) 2.2 (s, 3H), 4.85 (s, 2H), 7.25 (d, 1H), 7.6 (m, 3H), 7.8 (m, 2H), 7.95 (d, 2H), 8.05 (s, 1H), 8.16 (m, 2H), 9.96 (s, 1H), 10.44 (s, 1H); Mass M–H 445.

f) The product gave the following data: NMR (DMSOd$_6$) 0.97 (t, 3H), 2.2 (s, 3H), 2.35 (m, 10H), 3.53 (s, 2H), 7.23 (d, 1H), 7.42 (d, 2H) 7.59 (d, 1H), 7.78 (m, 2H), 7.93 (m, 3H), 8.26 (m, 2H); Mass M–H 524.

The N-[5-(3-trifluoromethylbenzamido)-2-methylphenyl]-4-chloromethylbenzamide used as a starting material was prepared as follows:

Triethylamine (1.6 ml) was added to a mixture of N-(3-amino-4-methylphenyl)-3-trifluoromethylbenzamide (3 g), 4-chloromethylbenzoyl chloride (2.9 g), 4-dimethylaminopyridine (0.125 g) and methylene chloride (50 ml) and the reaction mixture was stirred at ambient temperature for 16 hours. The mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. There was thus obtained the required compound as a solid (5.07 g); NMR (DMSOd$_6$) 2.21 (s, 3H), 4.84 (s, 2H), 7.25 (d, 1H), 7.57 (m, 3H), 7.76 (t, 1H), 7.83 (d, 1H), 7.96 (m, 3H), 8.26 (m, 2H), 9.92 (s, 1H), 10.44 (s, 1H); Mass M–H 445.

g) The product gave the following data: NMR (DMSOd$_6$) 2.14 (s, 3H), 2.2 (s, 3H), 2.36 (m, 8H), 3.51 (s, 2H), 7.23 (d, 1H), 7.46 (m, 2H), 7.58 (m, 1H), 7.84 (m, 3H), 8.0 (d, 2H), 8.1 (d, 2H); Mass M–H 467.

The N-[5-(4-cyanobenzamido)-2-methylphenyl]-3-chloromethylbenzamide used as a starting material was prepared as follows:

Triethylamine (1.83 ml) was added to a mixture of N-(3-amino-4-methylphenyl)-4-cyanobenzamide (3 g), 3-chloromethylbenzoyl chloride (2.48 g), 4-dimethylaminopyridine (0.146 g) and methylene chloride (50 ml) and the reaction mixture was stirred at ambient temperature for 16 hours. The mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. There was thus obtained the required compound as a solid (4.76 g); NMR (DMSOd$_6$) 2.2 (s, 3H), 4.84 (s, 2H), 7.24 (d, 1H), 7.55 (m, 2H), 7.66 (d, 1H), 7.83 (d, 1H), 8.0 (m, 4H), 8.1 (d, 2H), 9.96 (s, 1H), 10.46 (s 1H); Mass M–H 402.

h) The product gave the following data: NMR (DMSOd$_6$) 0.92 (d, 6H), 2.2 (s, 3H), 2.39 (m, 8H), 2.58 (m, 1H), 3.5 (s, 2H), 7.22 (d, 1H), 7.45 (m, 2H), 7.56 (d, 1H), 7.85 (m, 3H), 8.0 (d, 2H), 8.11 (d, 2H); Mass M–H 494.

The N-[5-(4-cyanobenzamido)-2-methylphenyl]-4-chloromethylbenzamide used as a starting material was prepared by the reaction of N-(3-amino-4-methylphenyl)-4-cyanobenzamide and 4-chloromethylbenzoyl chloride using an analogous procedure to that described in Note g) immediately hereinbefore.

i) The product gave the following data: NMR (DMSOd$_6$) 1.71 (br s, 4H), 2.2 (s, 3H), 2.46 (m, 4H), 3.63 (s, 2H), 7.23 (d, 1H), 7.47 (m, 2H), 7.59 (m, 1H), 7.85 (m, 3H), 7.99 (d, 2H), 8.12 (d, 2H); Mass M–H 437.

j) The product gave the following data: NMR (DMSOd$_6$) 2.2 (s, 3H), 2.38 (m, 4H), 3.52 (s, 2H), 3.58 (t, 4H), 7.13 (d, 1H), 7.5 (m, 3H), 7.85 (m, 3H), 8.0 (d, 2H), 8,1 (d, 2H); Mass M–H 453.

k) The product gave the following data: NMR (DMSOd$_6$) 1.38 (br s, 2H), 1.48 (br s, 4H), 2.2 (s, 3H), 2.32 (br s, 4H), 3.5 (s, 2H), 7.23 (d, 1H), 7.42 (d, 2H), 7.58 (d, 1H), 7.84 (s, 1H), 7.95 (d, 2H), 8.01 (d, 2H), 8.13 (d, 2H), 9.84 (br s, 1H), 10.47 (br s, 1H); Mass M–H 452.

l) The product gave the following data: NMR (DMSOd$_6$) 2.2 (s, 3H), 2.3 (m, 4H), 2.66 (m, 4H), 3.48 (s, 2H), 7.23 (d, 1H), 7.42 (d, 2H), 7.57 (d, 1H), 7.82 (s, 1H), 7.91 (d, 2H), 8.0 (d, 2H), 8.1 (d, 2H), 9.84 (s, 1H), 10.47 (s, 1H); Mass M–H 453.

m) The product gave the following data: NMR (DMSOd$_6$) 2.12 (s, 3H), 2.19 (s, 3H), 2.36 (m, 8H), 3.51 (s, 2H), 7.22 (d, 1H), 7.42 (d, 2H), 7.58 (m, 1H), 7.81 (d, 1H), 7.92 (d, 2H), 7.99 (d, 2H), 8.1 (d, 2H); Mass M–H 466.

EXAMPLE 29

N-[5-(2-Hydroxybenzamido)-2-methylphenyl]-3,4-dimethoxybenzamide

Using an analogous procedure to that described in Example 10, N-[5-(2-benzyloxybenzamido)-2-methylphenyl]-3,4-dimethoxybenzamide was hydrogenolysed to give the title compound in 92% yield;

NMR Spectrum: (DMSOd$_6$) 2.19 (s, 3H), 3.82 (s, 6H), 6.94 (m, 2H), 7.06 (d, 1H), 7.24 (d, 1H), 7.42 (t, 1H), 7.47 (m, 1H), 7.53 (d, 1H), 7.62 (m, 2H), 7.76 (d, 1H), 7.96 (m, 1H), 9.75 (br s, 1H), 10.35 (br s, 1H), 11.83 (br s, 1H); Mass Spectrum: M–H$^-$ 405.

The N-[5-(2-benzyloxybenzamido)-2-methylphenyl]-3,4-dimethoxybenzamide used as a starting material was obtained by the reaction of N-(5-amino-2-methylphenyl)-3,4-dimethoxybenzamide and 2-benzyloxybenzoyl chloride (obtained by the reaction of 2-benzyloxybenzoic acid and oxalyl chloride) using an analogous procedure to that described in Example 6. There was thus obtained the title compound in 64% yield; NMR Spectrum: (DMSOd$_6$) 2.13 (s, 3H), 3.83 (s, 6H), 5.24 (s, 2H), 7.11 (m, 3H), 7.26 (m, 3H), 7.52 (m, 4H), 7.63 (m, 2H), 7.71 (m, 1H), 7.86 (t, 2H), 9.73 (br s, 1H), 10.13 (d, 1H); Mass Spectrum: M+H$^+$ 497.

EXAMPLE 30

N-[5-(3-Dimethylaminobenzamido)-2-methylphenyl]-2-hydroxybenzamide

Using an analogous procedure to that described in Example 10, N-[5-(3-dimethylaminobenzamido)-2-methylphenyl]-2-benzyloxybenzamide was hydrogenolysed to give the title compound in 69% yield, m.p. 234–238° C.;

NMR Spectrum: (DMSOd$_6$) 2.22 (s, 3H), 2.97 (s, 6H), 6.92 (m, 3H), 7.21 (m, 3H), 7.3 (m, 1H), 7.42 (m, 1H), 7.57 (m, 1H), 8.02 (m, 1H), 8.21 (d, 1H), 10.15 (s, 1H), 10.38 (m, 1H); Mass Spectrum: M+H$^+$ 390.

The N-[5-(3-dimethylaminobenzamido)-2-methylphenyl]-2-benzyloxybenzamide used as a starting material was obtained by the reaction of N-(3-amino-4-methylphenyl)-3-dimethylaminobenzamide and 2-benzyloxybenzoyl chloride using an analogous procedure to that described in Example 7. There was thus obtained the title compound, m.p. 136–139° C.;

NMR Spectrum: (DMSOd$_6$) 1.85 (s, 1H), 2.98 (s, 6H), 5.36 (s, 2H), 6.9 (d, 1H), 7.12 (m, 2H), 7.33 (m, 7H), 7.52 (m, 4H), 7.9 (d, 1H), 8.12 (s, 1H), 9.7 (s, 1H), 10.08 (s, 1H); Mass Spectrum: M+H$^+$ 480.

EXAMPLE 31

N-[5-(3-Dimethylaminobenzamido)-2-methylphenyl]-3-aminobenzamide

10% Palladium-on-carbon (0.3 g) was added to a stirred suspension of N-[5-(3-dimethylaminobenzamido)-2-methylphenyl]-3-nitrobenzamide (2.25 g) in methanol (300 ml) and the mixture was stirred under an atmosphere of hydrogen. After cessation of hydrogen uptake the mixture was filtered and the filtrate was evaporated. The solid so obtained was dried under vacuum at 60° C. There was thus obtained the title compound (1.8 g); NMR Spectrum: (DMSOd$_6$) 2.18 (s, 3H), 2.95 (s, 6H), 5.26 (br s, 2H), 6.73 (m, 1H), 6.89 (m, 1H), 7.15 (m, 3H), 7.21 (m, 3H), 7.27 (m, 1H), 7.57 (m, 1H), 7.77 (d, 1H), 9.63 (br s, 1H), 10.07 (br s, 1H); Mass Spectrum: M+H$^+$ 390.

EXAMPLE 32

N-[5-(3-Dimethylaminobenzamido)-2-methylphenyl]-3-acetamidobenzamide

Acetyl chloride (0.066 g) was added to a stirred mixture of N-[5-(3-dimethylaminobenzamido)-2-methylphenyl]-3-aminobenzamide (0.3 g), triethylamine (0.22 ml) and methylene chloride (10 ml) and the mixture was stirred at ambient temperature for 60 hours. The mixture was washed with a saturated aqueous sodium bicarbonate solution and with water, dried (MgSO$_4$) and evaporated. The resultant solid was dried under vacuum at 60° C. There was thus obtained the title compound (0.243 g), m.p. 178–179° C.;

NMR Spectrum: (DMSO d$_6$) 2.05 (s, 3H), 2.19 (s, 3H), 2.95 (s, 6H), 6.9 (m, 1H), 7.24 (m, 3H), 7.29 (t, 1H), 7.42 (t, 1H), 7.57 (m, 1H), 7.61 (m, 1H), 7.79 (d, 1H), 7.81 (m, 1H), 8.09 (d, 1H), 9.86 (s, 1H), 10.09 (m, 2H); Mass Spectrum: M+H$^+$ 432.

EXAMPLE 33

N-[5-(3-Acetamidobenzamido)-2-methylphenyl]-3,4-dimethoxybenzamide

Using an analogous procedure to that described in Example 32, acetyl chloride was reacted with N-[5-(3-aminobenzamido)-2-methylphenyl]-3,4-dimethoxybenzamide to give the title compound in 69% yield, m.p. 187–188° C.;

NMR Spectrum: (DMSOd$_6$) 2.05 (s, 3H), 2.18 (s, 3H), 3.92 (s, 6H), 7.06 (d, 1H), 7.21 (d, 1H), 7.42 (t, 1H), 7.58 (m, 4H), 7.8 (m, 1H), 8.05 (m, 1H), 9.77 (s, 1H), 10.1 (s, 1H), 10.21 (s, 1H); Mass Spectrum: M+H$^+$ 448.

EXAMPLE 34

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph. Eur | 488.5 |
| Magnesium | 1.5 |
| (e) Injection I | (50 mg/ml) |
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

-continued

| (f) Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |
| (1 mg/ml, | |
| (g) Injection III | buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg/ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg/ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |
| (l) Ointment | ml |
| Compound X | 40 mg |
| Ethanol | 300 μl |
| Water | 300 μl |
| 1-Dodecylazacycloheptan-2-one | 50 μl |
| Propylene glycol | to 1 ml |

Note

The above formulations maybe obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A method of treating a disease or medical condition mediated by cytokines which comprises administering to a warm-blooded animal in need thereof an effective amount of a compound of the Formula I

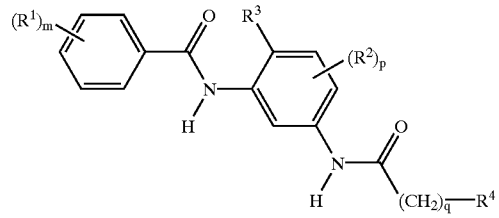

Formula I wherein:

$R^1$ and $R^2$, which may be the same or different are selected from hydroxy, $C_{1-6}$alkoxy, mercapto, $C_{1-6}$alkylthio, amino, $C_{1-6}$alkylamino, di-($C_{1-6}$alkyl) amino, carboxy, $C_{1-6}$alkoxycarbonyl, carbamoyl, $C_{1-6}$alkylcarbamoyl, di-$C_{1-6}$alkylcarbamoyl, $C_{1-6}$alkylsulphonyl, arylsulphonyl, $C_{1-6}$alkylaminosulphonyl, di-($C_{1-6}$alkyl) aminosulphonyl, nitro, cyano, cyano$C_{1-6}$alkyl, hydroxy$C_{1-6}$alkyl, amino$C_{1-6}$alkyl, $C_{1-6}$alkanoylamino, $C_{1-6}$alkoxycarbonylamino, $C_{1-6}$alkanoyl, $C_{1-6}$alkanoyloxy, $C_{1-6}$alkyl, halo, trifluoromethyl, aryl, aryl$C_{1-6}$alkyl and aryl$C_{1-6}$alkoxy;

m and p, are independently 0–3, and when m and/or p is 2 or 3 each R group may be the same or different;

$R^3$ is $C_{1-4}$alkyl;

q is 0;

$R^4$ is aryl or cycloalkyl wherein $R^4$ is optionally substituted with up to 3 substituents having any value defined for $R^1$;

or a pharmaceutically-acceptable salt or in vivo cleavable ester thereof.

2. The method of treatment as claimed in claim 1 wherein:

$R^1$ is hydroxy, methoxy, ethoxy, propoxy, isopropoxy, butoxy, amino, methylamino, dimethylamino, carboxy, methoxycarbonyl, nitro, cyano, acetamido, acetyl, acetoxy, methyl, ethyl, propyl, isopropyl, butyl, tert-butyl, fluoro, chloro, bromo or trifluoromethyl;

m is 1, 2 or 3;

p is 0;

$R^3$ is methyl;

q is 0; and $R^4$ is phenyl which is optionally substituted with 1 or 2 substituents selected from hydroxy, methoxy, ethoxy, amino, methylamino, dimethylamino, methoxycarbonyl, nitro, cyano, acetamido, fluoro, chloro, bromo, trifluoromethyl, phenyl and benzyloxy.

3. The method of treatment as claimed in claim 1 wherein:

$R^1$ is hydroxy, methoxy, ethoxy, propoxy, isopropoxy, butoxy, carboxy, methoxycarbonyl, nitro, cyano, acetamido, acetyl, methyl, ethyl, propyl, isopropyl, butyl, tert-butyl, fluoro, chloro, bromo or trifluoromethyl;

m is 0–3 and when m is 2 or 3 each $R^1$ group is the same or different;

p is 0;

$R^3$ is methyl;

q is 0; and $R^4$ is phenyl which is substituted at the 3- or 4-position with a substituent selected from amino, methylamino, dimethylamino and aminomethyl.

4. The method of treatment as claimed in claim 1 wherein:
$R^1$ is amino, methylamino, dimethylamino or aminomethyl;
m is 1 with the $R^1$ group located at the 3- or 4-position;
p is 0;
$R^3$ is methyl;
q is 0; and
$R^4$ is phenyl which is optionally substituted with 1 or 2 substituents, which may be the same or different, selected from hydroxy, methoxy, ethoxy, carboxy, methoxycarbonyl, cyano, methyl, fluoro, chloro and trifluoromethyl.

5. The method of treatment as claimed in claim 1 wherein:
$R^1$ is amino, methylamino, dimethylamino or aminomethyl;
m is 1 with the $R^1$ group located at the 3- or 4-position;
p is 0;
$R^3$ is methyl;
q is 0; and
$R^4$ is phenyl which is substituted at the 3- or 4-position with a substituent selected from amino, methylamino, dimethylamino and aminomethyl.

6. A compound of the Formula I

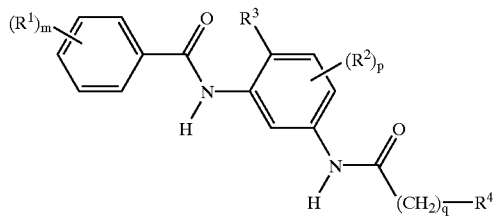

Formula I wherein:
$R^1$ is hydroxy, methoxy, ethoxy, propoxy, isopropoxy, butoxy, amino, methylamino, dimethylamino, carboxy, methoxycarbonyl, nitro, cyano, acetamido, acetyl, acetoxy, methyl, ethyl, propyl, isopropyl, butyl, tert-butyl, fluoro, chloro, bromo and trifluoromethyl;
m is 1, 2 or 3;
p is 0;
$R^3$ is methyl;
q is 0; and
$R^4$ is phenyl which is optionally substituted with 1 or 2 substituents selected from hydroxy, methoxy, ethoxy, amino, methylamino, dimethylamino, methoxycarbonyl, nitro, cyano, acetamido, fluoro, chloro, bromo, trifluoromethyl, phenyl and benzyloxy;
or a pharmaceutically-acceptable salt or in vivo cleavable ester thereof;
except that N-[5-(3-dimethylaminobenzamido)-2-methylphenyl]-4-hydroxybenzamide, N-[5-(2-hydroxybenzamido)-2-methylphenyl]-2-hydroxybenzamide, N-[5-(4-methoxybenzamido)-2-methylphenyl]-4-methoxybenzamide, N-[5-(3-methoxycarbonylbenzamido)-2-methylphenyl]-3-methoxycarbonylbenzamide and N-[5-(4-methoxycarbonylbenzamido)-2-methylphenyl]-4-methoxycarbonylbenzamide are excluded.

7. The compound according to claim 6 wherein:
$R^1$ is hydroxy, methoxy, ethoxy, isopropoxy, carboxy, methoxycarbonyl, nitro, cyano, acetyl, acetoxy, methyl, ethyl, propyl, fluoro, chloro or trifluoromethyl;
m is 1, 2 or 3;
p is 0;
$R^3$ is methyl;
q is 0; and
$R^4$ is phenyl which is optionally substituted with 1 or 2 substituents selected from hydroxy, methoxy, amino, methylamino dimethylamino, nitro, cyano, fluoro, chloro, bromo, trifluoromethyl and benzyloxy;
except that N-[5-(3-dimethylaminobenzamido)-2-methylphenyl]-4-hydroxybenzamide, N-[5-(2-hydroxybenzamido)-2-methylphenyl]-2-hydroxybenzamide and N-[5-(4-methoxybenzamido)-2-methylphenyl]-4-methoxybenzamide are excluded.

8. The compound according to claim 6 wherein:
$R^1$ is hydroxy, methoxy, carboxy or acetoxy;
m is 1 or 2;
p is 0;
$R^3$ is methyl;
q is 0; and
$R^4$ is phenyl which is optionally substituted with a substituent selected from hydroxy, dimethylamino, cyano and benzyloxy;
except that N-[5-(3-dimethylaminobenzamido)-2-methylphenyl]-4-hydroxybenzamide and N-[5-(2-hydroxybenzamido)-2-methylphenyl]-2-hydroxybenzamide are excluded.

9. A compound of the Formula I

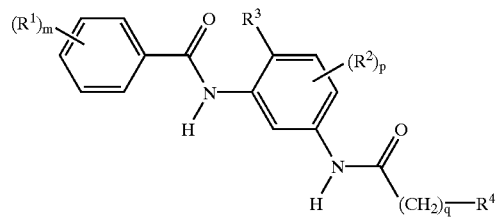

Formula I wherein:
$R^1$ is hydroxy, $C_{1-6}$alkoxy, carboxy, $C_{1-6}$alkoxycarbonyl, nitro, cyano, $C_{1-6}$alkanoylamino, $C_{1-6}$alkanoyl, $C_{1-6}$alkyl, halo or trifluoromethyl;
m is 0–3 and when m is 2 or 3 each $R^1$ group is the same or different;
p is 0;
$R^3$ is methyl;
q is 0; and
$R^4$ is phenyl which is substituted with 1 or 2 substituents selected from amino, $C_{1-6}$alkylamino, di-($C_{1-6}$alkyl)amino and amino$C_{1-6}$alkyl, and when there is 1 substituent it is located at the 3-position and when there are 2 substituents, which may be the same or different, they are located at the 3- and 4-positions;
or a pharmaceutically-acceptable salt or in vivo cleavable ester thereof;
except that N-[5-(3-dimethylaminobenzamido)-2-methylphenyl]-4-hydroxybenzamide is excluded.

10. The compound according to claim 9 wherein:

R$^1$ is hydroxy, methoxy, ethoxy, propoxy, isopropoxy, butoxy, carboxy, methoxycarbonyl, nitro, cyano, acetamido, acetyl, methyl, ethyl, propyl, isopropyl, butyl, tert-butyl, fluoro, chloro, bromo or trifluoromethyl;

m is 0–3 and when m is 2 or 3 each R$^1$ group is the same or different;

p is 0;

R$^3$ is methyl;

q is 0; and

R$^4$ is phenyl which is substituted at the 3- or 4-position with a substituent selected from amino, methylamino, dimethylamino and aminomethyl;

except that N-[5-(3-dimethylaminobenzamido)-2-methylphenyl]-4-hydroxybenzamide is excluded.

11. A compound of the Formula I

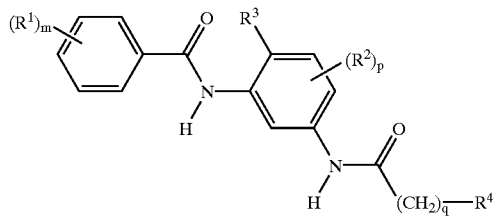

Formula I wherein:

R$^1$ is amino, C$_{1-6}$alkylamino, di-(C$_{1-6}$alkyl)amino or aminoC$_{1-6}$alkyl;

m is 1 with the R$^1$ group located at the 3-position or m is 2 with the R$^1$ groups, which may be the same or different, located at the 3- and 4-positions;

p is 0;

R$^3$ is methyl;

q is 0; and

R$^4$ is phenyl which is optionally substituted with 1 or 2 substituents, which may be the same or different, selected from hydroxy, C$_{1-6}$alkoxy, carboxy, C$_{1-6}$alkoxycarbonyl, cyano, C$_{1-6}$alkyl, halo and trifluoromethyl;

or a pharmaceutically-acceptable salt or in vivo cleavable ester thereof.

12. The compound according to claim 11 wherein:

R$^1$ is amino, methylamino, dimethylamino or aminomethyl;

m is 1 with the R$^1$ group located at the 3- or 4-position;

p is 0;

R$^3$ is methyl;

q is 0; and

R$^4$ is phenyl which is optionally substituted with 1 or 2 substituents, which may be the same or different, selected from hydroxy, methoxy, ethoxy, carboxy, methoxycarbonyl, cyano, methyl, fluoro, chloro and trifluoromethyl.

13. A compound of the Formula I

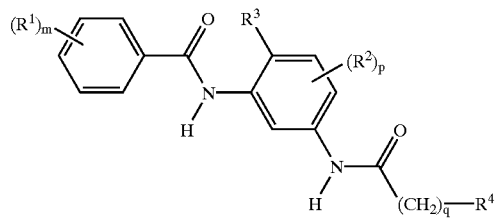

Formula I wherein:

R$^1$ is amino, C$_{1-6}$alkylamino, di-(C$_{1-6}$alkyl)amino or aminoC$_{1-6}$alkyl;

m is 1 with the R$^1$ group located at the 3-position or m is 2 with the R$^1$ groups, which may be the same or different, located at the 3- and 4-positions;

p is 0;

R$^3$ is methyl;

q is 0; and

R$^4$ is phenyl which is substituted with 1 or 2 substituents selected from amino, C$_{1-6}$alkylamino, di-(C$_{1-6}$alkyl)amino and aminoC$_{1-6}$alkyl, and when there is 1 substituent it is located at the 3-position and when there are 2 substituents, which may be the same or different, they are located at the 3- and 4-positions;

or a pharmaceutically-acceptable salt thereof.

14. The compound according to claim 13 wherein:

R$^1$ is amino, methylamino, dimethylamino or aminomethyl;

m is 1 with the R$^1$ group located at the 3- or 4-position;

p is 0;

R$^3$ is methyl;

q is 0; and

R$^4$ is phenyl which is substituted at the 3- or 4-position with a substituent selected from amino, methylamino, dimethylamino and aminomethyl.

15. A process for the preparation of a compound of the Formula I, or a pharmaceutically-acceptable salt or in vivo cleavable ester thereof, according to claim 6, 9, 11 or 13 which comprises:

(a) the reaction of a compound of the Formula III

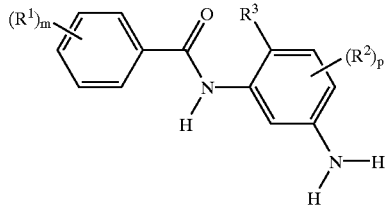

Formula III with a compound of the Formula IV

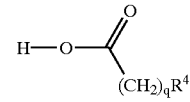

Formula IV or an activated derivative thereof, under standard amide bond firming conditions, wherein variable groups are as defined in claim 6, 9, 11 or 13 and wherein any functional group is protected, if necessary, and:
i. removing any protecting groups;
ii. optionally forming a pharmaceutically-acceptable salt or in vivo cleavable ester;

(b) the reaction of an acid of the Formula VI

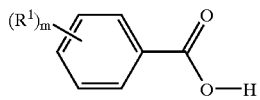

Formula VI or an activated derivative thereof, with an aniline of the Formula VIII Formula VIII under standard amide bond foil conditions, wherein variable groups are as defined in claim 6, 9, 11 or 13 and wherein any functional group is protected, if necessary, and:
i. removing any protecting groups;
ii. optionally forming a pharmaceutically-acceptable salt or in vivo cleavable ester;

(c) for the preparation of a compound of the Formula I according to claim 6, 9, 11 or 13 wherein $R^1$, $R^2$ or a substituent on $R^4$ is carboxy, the cleavage of a compound of the Formula I wherein $R^1$, $R^2$ or a substituent on $R^4$ is $C_{1-6}$alkoxycarbonyl;

(d) for the preparation of a compound of the Formula I according to claim 6, 9, 11 or 13 wherein $R^1$, $R^2$ or a substituent on $R^4$ is hydroxy, the cleavage of a compound of the Formula I wherein $R^1$, $R^2$ or a substituent on $R^4$ is benzyloxy or substituted benzyloxy;

(e) for the preparation of a compound of the Formula I according to claim 6, 9, 11 or 13 wherein $R^1$, $R^2$ or a substituent on $R^4$ is amino, the reduction of a compound of the Formula I wherein $R^1$, $R^2$ or a substituent on $R^4$ is nitro; or (f) for the preparation of a compound of the Formula I according to claim 6, 9, 11 or 13 wherein $R^1$, $R^2$ or a substituent on $R^4$ is $C_{1-6}$alkanoylamino, the acylation of a compound of the Formula I wherein $R^1$, $R^2$ or a substituent on $R^4$ is amino.

* * * * *